US010597347B2

(12) United States Patent
Chen et al.

(10) Patent No.: US 10,597,347 B2
(45) Date of Patent: Mar. 24, 2020

(54) NEO-ACIDS AND PROCESS FOR MAKING THE SAME

(71) Applicant: ExxonMobil Chemical Patents Inc., Baytown, TX (US)

(72) Inventors: Patrick C. Chen, Houston, TX (US); Kyle G. Lewis, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/033,298

(22) Filed: Jul. 12, 2018

(65) Prior Publication Data

US 2019/0100483 A1   Apr. 4, 2019

Related U.S. Application Data

(60) Provisional application No. 62/565,560, filed on Sep. 29, 2017.

(51) Int. Cl.
| *C07C 53/00* | (2006.01) |
| *C07C 51/00* | (2006.01) |
| *C07C 53/128* | (2006.01) |
| *C07C 51/14* | (2006.01) |
| *C07C 2/32* | (2006.01) |
| *B01J 21/02* | (2006.01) |
| *C07C 2/34* | (2006.01) |
| *B01J 31/14* | (2006.01) |
| *B01J 31/22* | (2006.01) |

(52) U.S. Cl.
CPC ............. *C07C 53/128* (2013.01); *B01J 21/02* (2013.01); *C07C 2/32* (2013.01); *C07C 2/34* (2013.01); *C07C 51/14* (2013.01); *B01J 31/143* (2013.01); *B01J 31/2295* (2013.01); *B01J 2231/20* (2013.01); *B01J 2531/48* (2013.01); *C07C 2521/06* (2013.01); *C07C 2531/14* (2013.01); *C07C 2531/22* (2013.01)

(58) Field of Classification Search
CPC ............................... C07C 53/128; C07C 51/14
See application file for complete search history.

(56) References Cited

U.S. PATENT DOCUMENTS

| 2,460,182 | A | 1/1949 | Geigy |
| 3,059,007 | A | 12/1962 | Vos et al. |
| 3,910,963 | A | 10/1975 | Souma et al. |
| 4,126,585 | A | 11/1978 | Conrad et al. |
| 4,332,738 | A | 6/1982 | Benitez et al. |
| 4,658,078 | A | 4/1987 | Slaugh et al. |
| 5,646,332 | A | 7/1997 | Cusumano et al. |
| 6,239,318 | B1 | 5/2001 | Schuler et al. |
| 2011/0084243 | A1 | 4/2011 | Cranor et al. |
| 2014/0011086 | A1 | 1/2014 | Fujdala et al. |
| 2015/0284350 | A1 | 10/2015 | Aruleswaran et al. |
| 2017/0183596 | A1 | 6/2017 | Ng et al. |
| 2018/0119045 | A1 | 5/2018 | Patil et al. |

FOREIGN PATENT DOCUMENTS

| DE | 10 2013 009323 | 12/2014 |
| EP | 0629603 | 12/1994 |
| EP | 2474537 | 7/2012 |
| JP | H0782216 | 3/1995 |
| WO | 2005/049542 | 6/2005 |

OTHER PUBLICATIONS

Sarnayskaya, et al., "Volatility and thermooxidation stability of synthetic ester oils ," Khimiya I Tekhnologiya Topliv I Masel, 1975; vol. 10, pp. 49-52 (Abstract).
Pincock et al,, "Alkylation of Ethyl, Isobornyl, and Menthyl Esters of 2-Methylbutanoic Acid ," Journal of Organic Chemistry, 1964, vol. 29, No. 10, pp. 299-2992.
Pirozhkov et al., "Synthesis of allyl esters of neo acids," Zhurnal Prikladnoi Khimii, 1976, vol. 49, No. 7, pp. 1646-1648 (Abstract).
Shapovalov, et al., "Radiation-induced telomerization of ethylene with methyl propionate," Deposited Doc., Viniti, 1975, vol. 32, No. 8, pp. 1628-1675 (Abstract).
Ye et al., "Nickel-catalyzed directed sulfenylation of sp2 and sp3 C—H bonds," Chemical Communications, 2015, vol. 51, No. 37, pp. 7863-7866.
Prout et al., "Unsymemetrical Quaternary Carbon Compounds. III. The Preparation and Resolution of Trialkylacetic Acids," Journal of Organic Chemistry, 1960, vol. 25, No. 5, pp. 835-838.
U.S. Appl. No. 15/988,716, filed May 24, 2018 Patil et al.
Didomenico et al.; "Compounds containing quaternary carbons, their use in medical devices, and methods," PCT Int. Appl., 2003.
Wagner-Jauregg et al., "Cycloalkyi aliphatic acids and their chemotherapeutic trial in leprosy and tuberculosis," Arb. Staatl. Inst. Exptl. Therap. U. Forsch.-Inst. Chemotherap. 1939, Frankfurt, No. 37, pp. 22-27, From: Chem. Zentr., 1939, II, pp. 459-460.
Mndzhoyan et al., "Derivatives of substituted acetic acids. XIX. Synthesis of .beta.-substituted phenylethyl esters of dialkylaminoacetic acids," Doklady Akademii Nauk Armyanskoi SSR, 1959, vol. 29, pp. 235-243.
Re et al., "Cyclization of 3-carboxy-3,6-dimethyl-1,5-heptadiene, a terpene acid with the skeleton of Artemisia ketone," Helvetica Chimica Acta, 1958, vol. 41, pp. 1695-1709.
U.S. Appl. No. 62/565,536, filed Sep. 29, 2017 Patil et al.
Kanth et al., "Selective Reduction of Carboxylic Acids into Alcohols Using NaBH4 and I2," J. Org. Chem., 1991, vol. 56, pp. 5964-5965.
Prasad et al., "Convenient Methods for the Reduction of Amides, Nitriles, Carboxylic Esters, Acids and Hydroboration of Alkenes Using NaBH4/I2 System," Tetrahedron, 1992, vol. 48, No. 22, pp. 4623-4628.
Jirosova et al., "Sphinganine-Like Biogenesis of (E)-1-Nitropentadec-1-ene in Termite Solders of the Genus Prorhinotermes," Chembiochem—a European Journal of Chemical Biology, 2014, vol. 15, No. 4, pp. 533-536.

(Continued)

*Primary Examiner* — Sikarl A Witherspoon
(74) *Attorney, Agent, or Firm* — John R. Wright; Siwen Chen

(57) ABSTRACT

This disclosure relates to neo-acids and processes for making neo-acids from a vinylidene olefin.

30 Claims, 1 Drawing Sheet

(56) References Cited

OTHER PUBLICATIONS

Luo et al., "Comparative study on aroma compounds in Chinese-type and Japanese-type soy sauces,", (2011).

Achonduh et al., "From alkenes to alcohols by cobalt-catalyzed hydroformylation-reduction," Tetrahedron, 2015, vol. 71, No. 8, pp. 1241-1246.

Cho et al., "Facile Reduction of Carboxylic Acids, Esters, Acid Chlorides, Amides and Nitriles to Alcohols or Amines Using NaBH4/BF3.Et20," Bulletin of the Korean Chemical Society, 2004, pp. 407-409.

Lebedev et al., "Synthesis of branched carboxylic acids with .alpha.-olefins and carbon monoxide in the presence of boron fluoride dehydrate," Neftepererabotka I Neftekhimiya, 1972, No. 8, pp. 7-11.

Polgar et al., "Long-Chain Acids Containing a Quaternary Carbon Atom, Part II," Journal of the American Chemical Society, 1943, pp. 615-619.

Delmau et al., "Combined Extraction of Cesium and Strontium from Alkaline Nitrate Solutions," Solvent Extraction and Ion Exchange, 2006, vol. 24, No. 2, pp. 197-217.

Rautenstrauch, "Potassium carboxylates by direct carbonylation of potassium alkoxides," Helvetica Chimica Acta, 1987, vol. 70, No. 3, pp. 593-599.

Newman, "alpha, alpha-Di-t-butyl-beta-propiolactone and Methyldi-t-butylacetic Acid from Di-t-butylketene," The Journal of Organic Chemistry, 1968, pp. 2144-2145.

Asano et al., "Syntheses of branched-chain fatty acids contained in tubercle bacilli. VI. Phthioic acid. 4," Yakugaku Zasshi, 1945, vol. 65, No. 4A, pp. 15-17.

Churilova et al., "Telomerization of propylene with carboxylic acids," Izvestiya Akademil Nauk SSSR, Seriya Khimicheskaya, 1975, vol. 11, pp. 2497-2501.

Stallberg-Stenhagen, "Optically active higher aliphatic compounds. XI. The synthesis of (-)-2-methyl-2-ethyleicosanoic acid," Arkiv Foci Kemi, 1951, vol. 3, pp. 273-280.

Bondareva et al., "Synthesis and extracting properties of triacylated ethyleneamines," Russian Journal of Applied Chemistry, 2011, vol. 84, No. 11, pp, 1897-1902.

Eidus et al., "Carbonylation of pentene-1 and 3-methylbutene-1 by carbon monoxide in the presence of hydrates of boron trifluoride," Bulletin of the Academy of Sciences of the USSR Division of Chemical Science, 1970, pp. 1585-1587.

U.S. Appl. No. 15/988,683, filed May 24, 2018 Chen et al.

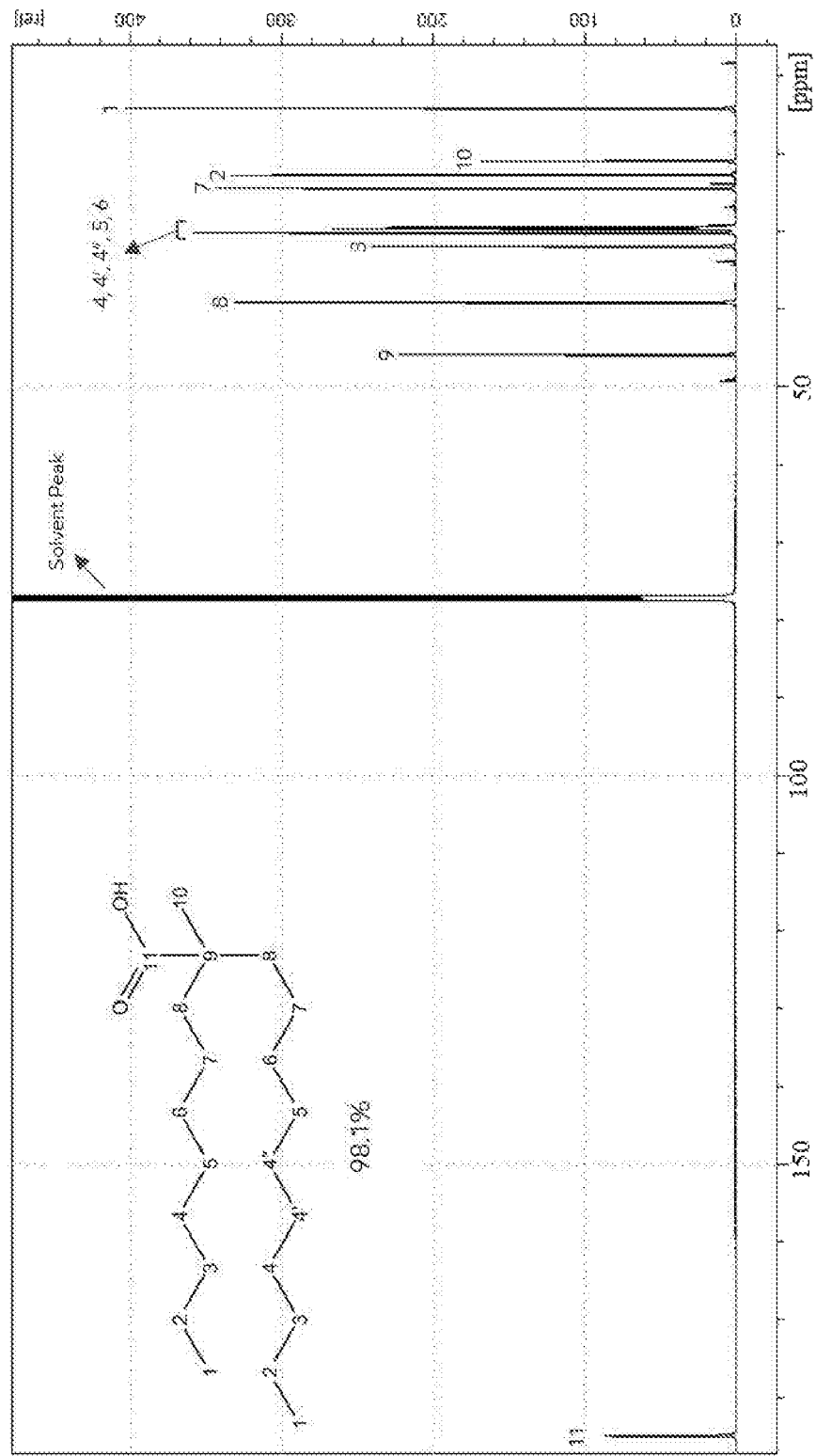

NEO-ACIDS AND PROCESS FOR MAKING THE SAME

PRIORITY CLAIM

This application claims priority to and the benefit of U.S. Ser. No. 62/565,560, filed Sep. 29, 2017, the content of which is incorporated herein by reference in its entirety.

FIELD OF THE DISCLOSURE

This disclosure relates to carboxylic acids and processes for making the same. In particular, this disclosure relates to neo-acid compounds and processes for making the same.

BACKGROUND OF THE DISCLOSURE

Neo-acids are carboxylic acids having the following general structure:

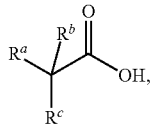

where $R^a$, $R^b$, and $R^c$ are independently hydrocarbyl groups. The quaternary carbon next to the carboxylic group makes it unique and interesting. A specific neo-acid, 2,2-dimethylpropanoic acid (corresponding to the above formula where $R^a$, $R^b$, and $R^c$ are methyl), has found use in many applications. This neo-acid can be made by carboxylation of isobutene via Koch reaction:

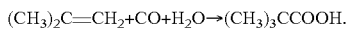

Neo-acids with at least one long carbon chain (i.e., a chain having a carbon backbone comprising at least 6 carbon atoms) may find use as intermediates for surfactants, lubricant base stocks, plasticizers, and the like.

Thus, there is a need for neo-acids having at least one long carbon chain and process for making such neo-acids.

This disclosure satisfy this and other needs.

SUMMARY OF THE DISCLOSURE

It has been found that a class of particularly useful neo-acids can be produced from reacting a vinylidene olefin with carbon monoxide in the presence of an acid catalyst. Such neo-acids can have one or two long carbon chains comprising at least 6 carbon atoms.

A first aspect of this disclosure relates to a compound having a formula (F-I) below:

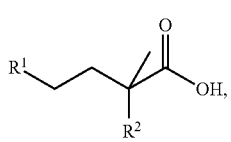

wherein $R^1$ and $R^2$ are each independently a hydrocarbyl group comprising at least two carbon atoms, provided $R^1$ and $R^2$ are not simultaneously ethyl or n-butyl.

A second aspect of this disclosure relates to a process for making a neo-acid product comprising a neo-acid compound having a formula (F-I) below:

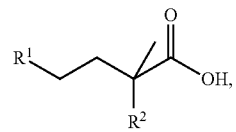

wherein $R^1$ and $R^2$ are each independently a hydrocarbyl group comprising at least two carbon atoms, the process comprising: (I) providing a vinylidene olefin feed comprising a vinylidene olefin having a formula (F-II) below:

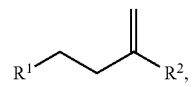

where $R^1$ and $R^2$ correspond to the $R^1$ and $R^2$ in formula (F-I) above, respectively; (II) contacting the vinylidene olefin with carbon monoxide in a reactor in the presence of an acid catalyst to obtain a reaction mixture; (III) contacting the reaction mixture with water to obtain an acid product mixture; and (IV) obtaining the neo-acid product from the acid product mixture.

Further features and advantages of this disclosure will be understood by reference to the following drawings and detailed description.

BRIEF DESCRIPTION OF THE DRAWING

The FIGURE is a $^{13}$C-NMR spectra of the neo-acid product made in Example B2 in this disclosure.

DETAILED DESCRIPTION OF THE DISCLOSURE

Definitions

In this disclosure, the indefinite article "a" or "an" means at least one, unless it is clearly specified or indicated by the context to mean one.

The term "alkyl group" or "alkyl" interchangeably refers to a saturated hydrocarbyl group consisting of carbon and hydrogen atoms. "Linear alkyl group" refers to a non-cyclic alkyl group in which all carbon atoms are covalently connected to no more than two carbon atoms. "Branched alkyl group" refers to a non-cyclic alkyl group in which at least one carbon atom is covalently connected to more than two carbon atoms. "Cycloalkyl group" refers to an alkyl group in which all carbon atoms form a ring structure comprising one or more rings.

The term "Hydrocarbyl group" or "hydrocarbyl" interchangeably refers to a group consisting of hydrogen and carbon atoms only. A hydrocarbyl group can be saturated or unsaturated, linear or branched, cyclic or acyclic, containing a cyclic structure or free of cyclic structure, and aromatic or non-aromatic. A "substituted" hydrocarbyl group is a hydrocarbyl group in which one or more hydrogen atom is substituted by any another group. An "unsubstituted" hydrocarbyl group is a hydrocarbyl group.

"Cn" group or compound refers to a group or a compound comprising carbon atoms at total number thereof of n. Thus, "Cm-Cn" or "Cm to Cn" group or compound refers to a group or compound comprising carbon atoms at a total number thereof in the range from m to n. Thus, a C1-C50 alkyl group refers to an alkyl group comprising carbon atoms at a total number thereof in the range from 1 to 50.

The term "carbon backbone" in an alkane or an alkyl group refers to the longest straight carbon chain in the molecule of the compound or the group in question.

The term "carbon backbone" of an olefin is defined as the straight carbon chain therein including a C=C functionality having the largest number of carbon atoms.

The term "olefin" refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be linear, branched linear, or cyclic.

The term "terminal olefin" refers to an olefin having a terminal carbon-to-carbon double bond in the structure thereof ((R$^1$R$^2$)—C=CH$_2$, where R$^1$ and R$^2$ can be independently hydrogen or any hydrocarbyl group, preferably R$^1$ is hydrogen, and R$^2$ is an alkyl group). A "linear terminal olefin" is a terminal olefin defined in this paragraph wherein R$^1$ is hydrogen, and R$^2$ is hydrogen or a linear alkyl group.

The term "vinyl" means an olefin having the following formula:

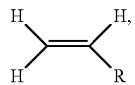

wherein R is a hydrocarbyl group, preferably a saturated hydrocarbyl group such as an alkyl group.

The term "vinylidene" means an olefin having the following formula:

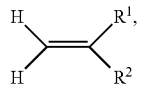

wherein R$^1$ and R$^2$ are each independently a hydrocarbyl group, preferably a saturated hydrocarbyl group such as alkyl group.

The term "1,2-di-substituted vinylene" means
(i) an olefin having the following formula:

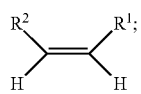

or
(ii) an olefin having the following formula:

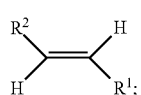

or
(iii) a mixture of (i) and (ii) at any proportion thereof, wherein R$^1$ and R$^2$ are each independently a hydrocarbyl group, preferably saturated hydrocarbyl group such as alkyl group.

The term "tri-substituted vinylene" means an olefin having the following formula:

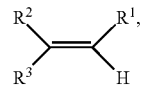

wherein R$^1$, R$^2$, and R$^3$ are each independently a hydrocarbyl group, preferably a saturated hydrocarbyl group such as alkyl group.

The term "polyalpha-olefin(s)" ("PAO(s)") includes any oligomer(s) and polymer(s) of one or more terminal olefin monomer(s). PAOs are oligomeric or polymeric molecules produced from the polymerization reactions of terminal olefin monomer molecules in the presence of a catalyst system, optionally further hydrogenated to remove residual carbon-carbon double bonds therein. Thus, the PAO can be a dimer (resulting from two terminal olefin molecules), a trimer (resulting from three terminal olefin molecules), a tetramer (resulting from four terminal olefin molecules), or any other oligomer or polymer comprising two or more structure units derived from one or more terminal olefin monomer(s). The PAO molecule can be highly regio-regular, such that the bulk material exhibits an isotacticity, or a syndiotacticity when measured by $^{13}$C-NMR. The PAO molecule can be highly regio-irregular, such that the bulk material is substantially atactic when measured by $^{13}$C-NMR. A PAO material made by using a metallocene-based catalyst system is typically called a metallocene-PAO ("mPAO"), and a PAO material made by using traditional non-metallocene-based catalysts (e.g., Lewis acids, supported chromium oxide, and the like) is typically called a conventional PAO ("cPAO"). A PAO material that has not been hydrogenated and therefore is unsaturated is called an unhydrogenated PAO ("uPAO").

The term "neo-acid" refers to a carboxylic acid having the following general structure:

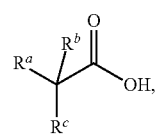

where R$^a$, R$^b$, and R$^c$ are independently hydrocarbyl groups.

The term "selectivity" of a terminal olefin in a reaction toward a given product species means the percentage of the terminal olefin converted into the given product species on the basis of all of the terminal olefin converted. Thus, if in a specific oligomerization reaction, 5% of the terminal olefin monomer is converted into trimer, then the selectivity of the terminal olefin toward trimer in the oligomerization reaction is 5%.

In this disclosure, all molecular weight data are in the unit of grams per mole (g·mol$^{-1}$).

NMR spectroscopy provides key structural information about the synthesized polymers. Proton NMR ($^1$H-NMR) analysis of the unsaturated PAO product gives a quantitative breakdown of the olefinic structure types (viz. vinyl, 1,2-di-substituted, tri-substituted, and vinylidene). In this disclosure, compositions of mixtures of olefins comprising terminal olefins (vinyls and vinylidenes) and internal olefins (1,2-di-substituted vinylenes and tri-substituted vinylenes) are determined by using $^1$H-NMR. Specifically, a NMR instrument of at least a 500 MHz is run under the following conditions: a 30° flip angle RF pulse, 120 scans, with a delay of 5 seconds between pulses; sample dissolved in CDCl$_3$ (deuterated chloroform); and signal collection temperature at 25° C. The following approach is taken in determining the concentrations of the various olefins among all of the olefins from an NMR spectrum. First, peaks corresponding to different types of hydrogen atoms in vinyls (Ti), vinylidenes (T2), 1,2-di-substituted vinylenes (T3), and tri-substituted vinylenes (T4) are identified at the peak regions in TABLE I below. Second, areas of each of the above peaks (A1, A2, A3, and A4, respectively) are then integrated. Third, quantities of each type of olefins (Q1, Q2, Q3, and Q4, respectively) in moles are calculated (as A1/2, A2/2, A3/2, and A4, respectively). Fourth, the total quantity of all olefins (Qt) in moles is calculated as the sum total of all four types (Qt=Q1+Q2+Q3+Q4). Finally, the molar concentrations (C1, C2, C3, and C4, respectively, in mol %) of each type of olefin, on the basis of the total molar quantity of all of the olefins, is then calculated (in each case, Ci=100*Qi/Qt).

TABLE I

| Type No. | Olefin Structure | Peak Region (ppm) | Peak Area | Number of Hydrogen Atoms | Quantity of Olefin (mol) | Concentration of Olefin (mol %) |
|---|---|---|---|---|---|---|
| T1 | CH$_2$=CH—R$^1$ | 4.95-5.10 | A1 | 2 | Q1 = A1/2 | C1 |
| T2 | CH$_2$=CR$^1$R$^2$ | 4.70-4.84 | A2 | 2 | Q2 = A2/2 | C2 |
| T3 | CHR$^1$=CHR$^2$ | 5.31-5.55 | A3 | 2 | Q3 = A3/2 | C3 |
| T4 | CR$^1$R$^2$=CHR$^3$ | 5.11-5.30 | A4 | 1 | Q4 = A4 | C4 |

All percentages in describing chemical compositions herein are by weight unless specified otherwise. "Wt %" means percent by weight.

"Consisting essentially of" means comprising at a concentration by weight of at least 90 wt %, based on the total weight of the mixture in question. Thus, an oligomerization product mixture consisting essentially of a dimer comprises dimer at a concentration by weight of at least 90 wt %, based on the total weight of the oligomerization product mixture.

All numerical values within the detailed description and the claims herein are modified by "about" or "approximately" the indicated value, taking into account experimental error and variations that would be expected by a person having ordinary skill in the art.

All kinematic viscosity values in this disclosure are as determined pursuant to ASTM D445. Kinematic viscosity at 100° C. is reported herein as KV100, and kinematic viscosity at 40° C. is reported herein as KV40. Unit of all KV100 and KV40 values herein is cSt unless otherwise specified.

All viscosity index ("VI") values in this disclosure are as determined pursuant to ASTM D2270.

The Neo-Acid Compound

One aspect of this disclosure is a novel category of compounds having a general formula (F-I) below:

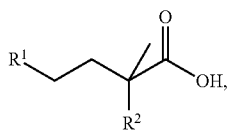

(F-I)

wherein R$^1$ and R$^2$ are each independently a hydrocarbyl group comprising at least two (2) carbon atoms (preferably a C2 to C60 hydrocarbyl group, more preferably a C2 to C60 alkyl group, still more preferably a C2 to C60 linear or branched alkyl group, and still more preferably a C2 to C30 linear or branched alkyl group), provided R$^1$ and R$^2$ are not both ethyl or n-butyl.

In formula (F-I), preferably R$^1$ and R$^2$ each independently comprise c1 to c2 carbon atoms, where c1 and c2 can be, independently, any integer from 2 to 60, such as 2, 3, 4, 5, 6, 7, 8, 9, 10, 12, 14, 16, 18, 20, 22, 24, 26, 28, 30, 32, 34, 36, 38, 40, 42, 44, 46, 48 50, 52, 54, 56, 58, or 60, as long as c1<c2. Preferably c1=2 and c2=30. More preferably c1=2 and c2=24. Still more preferably c1=4, and c2=16. Still more preferably c1=4, and c2=12. Preferably R$^1$ and R$^2$ each independently comprise even number of carbon atoms.

At least one of R$^1$ and R$^2$ (preferably both R$^1$ and R$^2$ independently each) can be a branched alkyl group, preferably a branched alkyl group having the following formula (F-IV):

(F-IV)

where R$^a$ and R$^b$ are independently hydrocarbyl groups, preferably alkyl groups, more preferably linear or branched alkyl groups, still more preferably linear alkyl groups, m is a non-negative integer, preferably m≥2, more preferably m≥3, still more preferably m≥4, still more preferably m≥5, still more preferably m≥6, still more preferably m≥7. Preferably R$^a$ and R$^b$ independently comprises c3 to c4 carbon atoms, where c3 and c4 can be, independently, any integer from 1 to 57, such as 1, 2, 3, 4, 5, 6, 7, 8, 9, 10, 12, 14, 16, 18, 20, 22, 23, 24, 26, 28, 30, 32, 34, 36, 38, 40, 42, 44, 46, 48 50, 52, 54, 56, or 57, as long as c3<c4. More preferably c3=1 and c4=50. Still more preferably c3=1 and c4=40. Still more preferably c3=1 and c4=20. Still more preferably c3=1 and c4=16. Still more preferably c3=1, and c4=10. In one specific embodiment, m=0 and R$^1$ and/or R$^2$ can be a group branched at the 1-location, i.e., the carbon directly connected to the quaternary carbon atom. Non-limiting examples of branched alkyls for R$^1$ and R$^2$ include: 2-ethylhexyl, 2-propylheptanyl, 2-butyloctyl, and 3,5-dimethyloctyl.

At least one of R$^1$ and R$^2$ (preferably both R$^1$ and R$^2$ independently) can be linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. Preferably the total number of carbon atoms in linear $R^1$ and $R^2$ is an even number. Preferably the total number of carbon atoms in the linear $R^1$ and/or $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as a1<a2. Preferably the total number of carbon atoms in the linear $R^1$ and $R^2$ combined is from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably the total number of carbon atoms in $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as b1<b2. Preferably the total number of carbon atoms in $R^1$ and $R^2$ is in a range from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably $R^1$ and $R^2$ are identical. In such case, it is particularly preferred that $R^1$ and $R^2$ contain even number of carbon atoms. It is also particularly preferred that $R^1$ and $R^2$ are identical linear alkyl groups. Where $R^1$ and $R^2$ in formula (F-I) differ, it is highly desirable that they differ in terms of molar mass thereof by no greater than 145 (or 130, 115, 100, 85, 70, 55, 45, 30, or even 15) grams per mole. Preferably in such cases $R^1$ and $R^2$ differ in terms of total number of carbon atoms contained therein by no greater than 10 (or 9, 8, 7, 6, 5, 4, 3, 2, or even 1).

Particularly desirable examples of the neo-acid compounds of this disclosure are as follows: 2-methyl-2-propylheptanoic acid; 2-butyl-2-methylhexanoic acid; 2-ethyl-2-methyloctanoic acid; 2-butyl-2-methyloctanoic acid; 2-butyl-2-methyldecanoic acid; 2-hexyl-2-methyloctanoic acid; 2-hexyl-2-methyldecanoic acid; 2-methyl-2-octyldecanoic acid; 2-hexyl-2-methyldodecanoic acid; 2-methyl-2-octyldodecanoic acid; 2-decyl-2-methyldodecanoic acid; 2-decyl-2-methyltetradecanoic acid; 2-methyl-2-octyltetradecanoic acid; 2-dodecyl-2-methyltetradecanoic acid; 2-dodecyl-2-methylhexadecanoic acid; 2-decyl-2-methylhexadecanoic acid; 2-methyl-2-tetradecylhexadecanoic acid; 2-methyl-2-tetradecyloctadecanoic acid; 2-dodecyl-2-methyloctadecanoic acid; 2-methyl-2-tetradecylicosanoic acid; 2-hexadecyl-2-methylicosanoic acid; and 2-hexadecyl-2-methyloctadecanoic acid.

Process for Making the Neo-Acid Compound and/or Neo-Acid Product

Another aspect of this disclosure relates to a process for making a neo-acid product comprising a neo-acid compound having a formula (F-I) below:

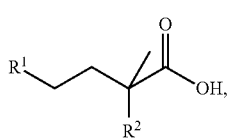

(F-I)

wherein: $R^1$ and $R^2$ are each independently a hydrocarbyl group comprising at least two (2) carbon atoms (preferably a C2-C60 hydrocarbyl group, more preferably a C2-C60 alkyl group, still more preferably a C2-C60 linear or branched alkyl group, still more preferably a C2 to C30 linear or branched alkyl group); preferably $R^1$ and $R^2$ are not both ethyl or n-butyl), the process comprising:

(I) providing a vinylidene olefin feed comprising a vinylidene olefin having a formula (F-II) below:

(F-II)

where $R^1$ and $R^2$ correspond to the $R^1$ and $R^2$ in formula (F-I) above, respectively;

(II) contacting the vinylidene olefin with carbon monoxide in a reactor in the presence of an acid catalyst at a carbon monoxide partial pressure of at least 3.5 MPa to obtain a reaction mixture;

(III) contacting the reaction mixture with water to obtain an acid product mixture; and (IV) obtaining the neo-acid product from the acid product mixture.

I. The Vinylidene Olefin Feed and Processes for Making the Same

I.1 General

The vinylidene olefin useful in the process of this disclosure for making the neo-acid product has a formula (F-II) below:

(F-II)

wherein $R^1$ and $R^2$ are each independently a hydrocarbyl group comprising at least two (2) carbon atoms (preferably a C2-C60 hydrocarbyl group, more preferably a C2-C60 alkyl group, still more preferably a C2-C60 linear or branched alkyl group, still more preferably a C2 to C30 linear or branched alkyl group). To the extent this compound can be considered as a dimer derived from to molecules of terminal olefin(s), it will be referred to as a terminal olefin dimer or a vinylidene dimer of terminal olefin(s) in this disclosure.

In formula (F-II), preferably $R^1$ and $R^2$ each independently comprise c1 to c2 carbon atoms, where c1 and c2 can be, independently, any integer from 2 to 60, such as 2, 3, 4, 5, 6, 7, 8, 9, 10, 12, 14, 16, 18, 20, 22, 24, 26, 28, 30, 32, 34, 36, 38, 40, 42, 44, 46, 48 50, 52, 54, 56, 58, or 60, as long as c1<c2. Preferably c1=2 and c2=30. More preferably c1=2 and c2=24. Still more preferably c1=4, and c2=16. Still more preferably c1=4, and c2=12. Preferably $R^1$ and $R^2$ each independently comprise even number of carbon atoms.

At least one of $R^1$ and $R^2$ (preferably both $R^1$ and $R^2$ independently each) can be a branched alkyl group, preferably a branched alkyl group having the following formula (F-IV):

(F-IV)

where $R^a$ and $R^b$ are independently hydrocarbyl groups, preferably alkyl groups, more preferably linear or branched alkyl groups, still more preferably linear alkyl groups, m is a non-negative integer, preferably m≥2, more preferably m≥3, still more preferably m≥4, still more preferably m≥5, still more preferably m≥6, still more preferably m≥7. Preferably $R^a$ and $R^b$ independently comprises c3 to c4 carbon atoms, where c3 and c4 can be, independently, any integer from 1 to 57, such as 1, 2, 3, 4, 5, 6, 7, 8, 9, 10, 12, 14, 16, 18, 20, 22, 23, 24, 26, 28, 30, 32, 34, 36, 38, 40, 42, 44, 46, 48 50, 52, 54, 56, or 57, as long as c3<c4. More preferably c3=1 and c4=50. Still more preferably c3=1 and c4=40. Still more preferably c3=1 and c4=20. Still more preferably c3=1 and c4=16. Still more preferably c3=1, and c4=10. In one specific embodiment, m=0 and $R^1$ and/or $R^2$ can be a group branched at the 1-location, i.e., the carbon directly connected to the quaternary carbon atom. Non-limiting examples of branched alkyls for $R^1$ and $R^2$ include: 2-ethylhexyl, 2-propylheptanyl, 2-butyloctyl, and 3,5-dimethyloctyl.

At least one of $R^1$ and $R^2$ (preferably both $R^1$ and $R^2$ independently) can be linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. Preferably the total number of carbon atoms in linear $R^1$ and $R^2$ is an even number. Preferably the total number of carbon atoms in the linear $R^1$ and/or $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as a1<a2. Preferably the total number of carbon atoms in the linear $R^1$ and $R^2$ combined is from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably the total number of carbon atoms in $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as b1<b2. Preferably the total number of carbon atoms in $R^1$ and $R^2$ is in a range from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably $R^1$ and $R^2$ are identical. In such case, it is particularly preferred that $R^1$ and $R^2$ contain even number of carbon atoms. It is also particularly preferred that $R^1$ and $R^2$ are identical linear alkyl groups. Where $R^1$ and $R^2$ in formula (F-I) differ, it is highly desirable that they differ in terms of molar mass thereof by no greater than 145 (or 130, 115, 100, 85, 70, 55, 45, 30, or even 15) grams per mole. Preferably in such cases $R^1$ and $R^2$ differ in terms of total number of carbon atoms contained therein by no greater than 10 (or 9, 8, 7, 6, 5, 4, 3, 2, or even 1).

The vinylidene olefin having formula (F-II) can be advantageously made by dimerization of a monomer feed comprising a terminal olefin having a formula (F-III) below and optionally a terminal olefin having a formula (F-IV) below: $R^1$—CH=CH$_2$ (F-III), $R^2$—CH=CH$_2$ (F-IV). It is highly desirable that the monomer feed consists essentially of a single terminal olefin having a formula (F-III). In such case a single vinylidene olefin having a formula (F-II) where $R^1$ and $R^2$ are identical can be advantageously made in the dimerization process, which can be used as the vinylidene olefin feed in step (I) of the process of this disclosure for making a neo-acid product. It is contemplated that the monomer feed may comprise multiple terminal olefins having differing formulas (F-III). In such case, as discussed below, multiple vinylidene olefins having different formulas (F-II) may be produced in the dimerization reaction, which can be used together as the vinylidene olefin feed for making a neo-acid product comprising multiple neo-acid compounds. Where the monomer feed comprises multiple terminal olefins, it is highly desirable that they differ in terms of molecular weight thereof by no greater than 145 (or 130, 115, 100, 85, 70, 55, 45, 30, or even 15) grams per mole. Preferably in such cases the multiple terminal olefins contained in the monomer feed differ in terms of total number of carbon atoms contained therein by no greater than 10 (or 9, 8, 7, 6, 5, 4, 3, 2, or even 1).

Such dimerization can be carried out advantageously in the presence of a catalyst system comprising a metallocene compound. U.S. Pat. No. 4,658,078 discloses a process for making a vinylidene olefin dimer from a terminal olefin monomer, the content of which is incorporated herein by reference in its entirety. The batch processes as disclosed in U.S. Pat. No. 4,658,078 resulted in the production of trimers and higher oligomers at various levels along with the intended dimer, which can be removed by, e.g., distillation, to obtain a substantially pure dimer product. The dimer product made in the batch processes of U.S. Pat. No. 4,658,078 may contain 1,2-di-substituted vinylene(s) and tri-substituted vinylenes at various levels. To the extent the concentrations of the 1,2-di-substituted vinylene(s) and tri-substituted vinylenes are acceptable to the intended application of this disclosure, the batch processes as disclosed in U.S. Pat. No. 4,658,078 may be used to produce the dimer having formula (F-II) above useful in the process for making the neo-acid product in tis disclosure.

Such dimerization can also be carried out in the presence of trialkylaluminum such as tri(tert-butyl)aluminum as disclosed in U.S. Pat. No. 4,987,788, the content of which is incorporated by reference in its entirety.

Desirably the vinylidene olefin having formula (F-II) feed used in the process of this disclosure for making neo-acid product comprises a single vinylidene olefin having formula (F-II) having a purity thereof of at least 90 wt %, preferably at least 92 wt %, more preferably at least 94 wt %, still preferably at least 95 wt %, still more preferably 96 wt %, still more preferably at least 97 wt %, still more preferably at least 98 wt %, still more preferably at least 99 wt %, based on the total weight of the olefins contained in the feed.

It is possible to use a mixture of two or more vinylidene olefins having different formulae (F-II) as the vinylidene olefin feed in the process for making a mixture of neo-acid products as the neo-acid product. Desirably, the individual vinylidene olefins contained in the mixture have similar molecular weights, i.e., having molecular weights that differ by no more than, e.g., 145, 130, 115, 100, 85, 70, 55, 45, 30, or even 15 grams per mole. Desirably, the individual vinylidene olefins contained in the mixture differ in terms of total number of carbon atoms contained therein by no more than 10, 9, 8, 7, 6, 5, 4, 3, 2, or even 1. The individual vinylidene olefins contained in the mixture can be structural isomers. The vinylidene olefins having different chemical formulas and/or molecular weight can be converted into neo-acid compounds having different chemical formulas and/or molecular weight under the same reaction conditions following the same reaction mechanism. As long as the mixture of neo-acid compounds can be used for the intended application, the corresponding mixture of vinylidene olefin can be used as the vinylidene olefin feed for making the neo-acid product by using the process of this disclosure.

It is highly desirable that the vinylidene olefin feed used in the process of this disclosure for making neo-acid product comprises 1,2-di-substituted vinylene(s) and tri-substituted vinylene(s) as impurities at a total concentration no greater than 5 wt %, preferably no greater than 4 wt %, still more preferably no greater than 3 wt %, still more preferably no greater than 2 wt %, still no greater than 1 wt %, based on the total weight of olefins contained in the feed.

Non-limiting, particularly desirable examples of vinylidene olefins for the process for making neo-acid products of this disclosure include: 3-methylenepentane; 4-methylenenonane; 3-methylenenonane; 5-methyleneundecane; 5-methylenetridecane; 7-methylenetridecane; 7-methylenepentadecane; 9-methyleneheptadecane; 7-methyleneheptadecane; 9-methylenenonadecane; 11-methylenehenicosane; 11-methylenetricosane; 9-methylenehenicosane; 13-methylenepentacosane; 13-methyleneheptacosane; 11-methylenepentacosane; 15-methylenenonacosane; 15-methylenehentriacontane; 13-methylenenonacosane; 15-methylenetritriacontane; 17-methylenepentatriacontane; 17-methylenetritriacontane; and mixtures thereof. Preferred mixtures are those having total number of carbon atoms in the molecules thereof no greater than 8, preferably no greater than 6, still more preferably no greater than 4, still more preferably no greater than 2. The following vinylidene olefins are preferred, especially as a high-purity, single vinylidene olefin feed: 4-methylenenonane; 5-methyleneundecane; 6-methylenetridecane; 7-methylenepentadecane; 8-methyleneheptadecane; 9-methylenenonadecane; 11-methylenetricosane; 13-methyleneheptacosane; 15-methylenehentriacontane; 17-methyleneheptatriacontane; and 19-methylenenonatriacontane.

Detailed description of a preferred process for making vinylidene olefin feed suitable for the process for making neo-acid of this disclosure are given below.

I.2 Continuous Process for Making High-Purity Vinylidene Olefin Using a Catalyst System Comprising a Metallocene Compound However, a particularly desirable process for a vinylidene olefin dimer product from a terminal olefin feed for use in the process of this disclosure is continuous, as opposed to a batch process such as those disclosed in U.S. Pat. No. 4,658,078. The oligomerization (dimerization being one) reaction can therefore be carried out in a continuously operated reactor, such as a continuously stirred tank reactor, a plug flow reactor or a loop reactor. Quite surprisingly, it was found that in a continuous process, one can achieve an extremely high selectivity toward dimer of the terminal olefin monomer and avoid the production of high quantity of trimer and higher oligomer.

This continuous process represents a significant improvement to the processes disclosed in U.S. Pat. No. 4,658,078, as it results in the production of a high-purity vinylidene olefin dimer of the terminal olefin dimer. The oligomerization reaction pursuant to the continuous process features an exceedingly high selectivity toward dimer and exceedingly low selectivity toward trimers and higher oligomers and an exceedingly high selectivity toward vinylidene olefin dimer as opposed to 1,2-di-substituted vinylene and tri-substituted vinylene. Thus, the oligomer mixture obtained from the oligomerization step, upon removal of residual terminal olefin monomer and catalyst, can be used directly as a high-purity vinylidene olefin dimer for the process of making a neo-acid product of this disclosure. In addition, the oligomerization reaction can be carried out with a high conversion of the terminal olefin monomer. Moreover, the oligomerization reaction of the continuous process results in little isomerization of the terminal olefin monomer, the dimer, and other oligomers. Therefore, the residual terminal olefin monomer contained in the oligomerization reaction mixture can be separated and recycled to the oligomerization reaction. Last but not least, the oligomerization reaction in the continuous process is carried out under mild, steady conditions in a continuous fashion, resulting in a vinylidene olefin dimer intermediate with consistent composition and quality, which, in turn, can be used for making a gamma-alcohol product with high purity.

I.2a the Terminal Olefin

The terminal olefin monomer useful in the continuous process for making the vinylidene olefin having formula (F-II) can desirably comprise from n1 to n2 carbon atoms per molecule, where n1 and n2 can be, independently, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, 60, as long as $n1<n2$. Preferably $n1=4$ and $n2=50$; more preferably $n1=6$ and $n2=40$; still more preferably $n1=6$ and $n2=30$; still more preferably $n1=6$ and $n2=20$.

Preferred terminal olefin monomers are mono-olefins containing one C=C bond per monomer molecule, though those olefins containing two or more C=C bonds per monomer molecule can be used as well.

The terminal olefin monomer useful in the continuous process for making the vinylidene olefin having formula (F-II) can be preferably a linear terminal olefin. Particularly useful examples of linear terminal olefins as the monomer for the process of this disclosure are: 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-icosene, 1-henicosene, 1-docosene, 1-tricosene, 1-tetracosene, 1-pentacosene, 1-hexacosene, 1-heptacosene, 1-octacosene, 1-nonacosene, and 1-triacontene. Preferred examples of linear terminal olefins as the monomer for the process of this disclosure are: 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-icosene. Still more preferred linear terminal olefin as monomer for the process of this disclosure are: 1-pentene, 1-hexene, 1-octene, 1-decene, 1-dodecene, 1-tetradecene, 1-hexadecene, 1-octadecene, and 1-icosene. Still more preferred linear terminal olefins as monomer for the process of this disclosure are: 1-hexene, 1-octene, 1-decene, 1-dodecene, 1-tetradecene, 1-hexadecene, and 1-octadecene. Linear terminal olefins having even number of carbon atoms can be advantageously manufactured by the oligomerization of ethylene, as is typically done in the industry. Many of these linear terminal olefins with even number of carbon atoms are commercially available at large quantities.

Branched terminal olefins can be used as the monomer in the process as well. Particularly useful branched terminal olefins are those represented by the following formula:

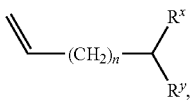

where $R^x$ and $R^y$ are independently any hydrocarbyl group, preferably any C1-C30 alkyl group, more preferably any C1-C30 linear alkyl group, n is a non-negative integer, preferably n≥2, more preferably n≥4, and still more preferably n≥5. Preferably n≤30, more preferably n≤20, still more preferably n≤15. Where n=0, the terminal olefin per se represents a vinylidene olefin, which can be a vinylidene olefin described above, and can be made from terminal olefins through dimerization of terminal olefin(s) monomer described here.

The terminal olefin monomer may be fed as a pure material or as a solution in an inert solvent into the continuously operated oligomerization reactor. Non-limiting examples of the inert solvent include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

The terminal olefins used herein can be produced directly from ethylene growth process as practiced by several commercial production processes, or they can be produced from Fischer-Tropsch hydrocarbon synthesis from CO/H$_2$ syngas, or from metathesis of internal olefins with ethylene, or from cracking of petroleum or Fischer-Tropsch synthetic wax at high temperature, or any other terminal olefin synthesis routes. A preferred feed for this invention is preferably at least 80 wt % terminal olefin (preferably linear alpha olefin), preferably at least 90 wt % terminal olefin (preferably linear alpha olefin), more preferably 100% terminal olefin (preferably linear alpha olefin). The feed olefins can be the mixture of olefins produced from other linear terminal olefin process containing C4 to C20 terminal olefins as described in Chapter 3 "Routes to Alpha-Olefins" of the book Alpha Olefins Applications Handbook, Edited by G. R. Lappin and J. D. Sauer, published by Marcel Dekker, Inc. N.Y. 1989.

The terminal olefin feed and or solvents may be treated to remove catalyst poisons, such as peroxides, oxygen or nitrogen-containing organic compounds or acetylenic compounds before being supplied to the polymerization reactor. The treatment of the linear terminal olefin with an activated 13 Angstrom molecular sieve and a de-oxygenate catalyst, i.e., a reduced copper catalyst, can increase catalyst productivity (expressed in terms of quantity of PAO produced per micromole of the metallocene compound used) more than 10-fold. Alternatively, the feed olefins and or solvents are treated with an activated molecular sieve, such as 3 Angstrom, 4 Angstrom, 8 Angstrom or 13 Angstrom molecular sieve, and/or in combination with an activated alumina or an activated de-oxygenated catalyst. Such treatment can desirably increase catalyst productivity 2- to 10-fold or more.

Where a substantially pure dimer compound

a vinylidene olefin having a formula (F-II) where $R^1$ and $R^2$ are identically R) is desirable, a single terminal olefin monomer (R—CH=CH$_2$) can be fed into the oligomerization reactor. Thus, a pure 1-octene feed will result in a single C16 dimer vinylidene olefin (7-methylenepentadecane), a pure 1-decene feed will result in a single C20 dimer vinylidene olefin (9-methylenenonadecane), a pure 1-dodecene feed will result in a single C24 dimer vinylidene olefin (11-methylenetricosane), a pure 1-tetradecene feed will result in a single C28 dimer vinylidene olefin (13-methyleneheptacosane).

If two different terminal olefin monomers including a first monomer ($R^a$—CH=CH$_2$) and a second monomer ($R^b$—CH=CH$_2$, where $R^b$ differs from $R^a$) are fed into the oligomerization reactor, multiple different dimer compounds may be produced at various quantities depending on the dimerization reactivity of them: a first dimer formed from two units of the first monomer

corresponding to a vinylidene olefin having a formula (F-II) where $R^1$ and $R^2$ groups are identical $R^a$); a second dimer formed from two units of the second monomer

corresponding to a vinylidene olefin having a formula (F-II) where $R^1$ and $R^2$ are identical $R^b$), and a third category of dimers formed from one unit of the first monomer and another unit of the second monomer

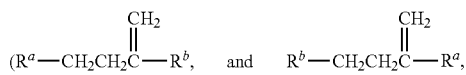

corresponding to vinylidene olefins having formula (F-II) where $R^1$ and $R^2$ are different). The third category of dimers can have multiple isomers as shown. By way of example, a terminal olefin feed consisting of 1-decene and 1-dodecene in the continuous process for making the vinylidene olefin having formula (F-II) results in the production of a dimer mixture comprising 9-methylenenonadecane, 9-methylenehenicosane, 11-methylenehenicosane, and 11-methylenetricosane. To the extent such a dimer mixture is acceptable for the intended application, a mixture of two (or even more) terminal olefin may be used as a terminal olefin feed into the oligomerization reactor. In commercial productions, even a high-purity terminal olefin feed invariably contains impurities such as other terminal olefins at various concentrations in addition to the predominant terminal olefin. As a result, various quantities of multiple minor vinylidene olefin dimer olefins may be produced in addition to the intended predominant dimer of the predominant terminal olefin. To the extent the presence of such minor vinylidene dimer olefins at the specific quantities does not interfere with the intended use of the dimer product, such terminal olefin feed comprising minor quantities of other terminal olefin(s) than the predominant terminal olefin can be tolerated in the continuous process for making the vinylidene olefin having formula (F-II).

I.2b The Metallocene Compound

The metallocene compound in the catalyst system useful in the continuous process for making the vinylidene olefin having formula (F-II) can be represented by the formula $Cp(Bg)_nMX_2Cp'$, where Cp and Cp', the same or different, represents a cyclopentadienyl, alkyl-substituted cyclopentadienyl, indenyl, alkyl-substituted indenyl, 4,5,6,7-tetrahydro-2H-indenyl, alkyl-substituted 4,5,6,7-tetrahydro-2H-indenyl, 9H-fluorenyl, and alkyl-substituted 9H-fluorenyl; Bg represents a bridging group covalently linking Cp and Cp', and n is zero (0), one (1), or two (2), preferably zero (0) or one (1), more preferably zero (0, i.e., where the metallocene compound is unbridged). Exemplary Bg can be represented by any of

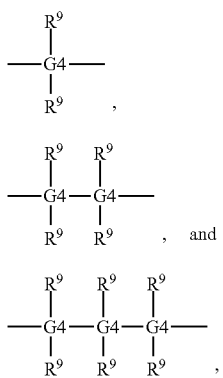

where groups G4 are, the same or different at each occurrence, independently selected from carbon, silicon, and germanium, and each $R^9$ is independently a C1-C30 substituted or unsubstituted linear, branched, or cyclic hydrocarbyl groups. Preferred $R^9$ includes substituted or unsubstituted methyl, ethyl, n-propyl, phenyl, and benzyl. Preferably Bg is category (i) or (ii) above. More preferably Bg is category (i) above. Preferably all $R^9$'s are identical.

M represents Hf or Zr. Preferably M is Zr. X, the same or different at each occurrence, independently represents a halogen such as Cl or a hydrocarbyl such as: linear or branched alkyl group such as methyl, ethyl, n-propyl, isopropyl, n-butyl and branched isomeric group thereof, n-pentyl and branched isomeric group thereof, n-hexyl and branched isomeric group thereof, n-heptyl and branched isomeric group thereof, n-octyl and branched isomeric group thereof, n-nonyl and branched isomeric group thereof, n-decyl and branched isomeric group thereof, and the like; a cycloalkyl group; a cycloalkylalkyl group; an alkylcycloalkyl group; an aryl group such as phenyl; an arylalkyl group such as benzyl; an alkylaryl group such as tolyl and xylyl. Preferably X is methyl or Cl; more preferably X is Cl. Without intending to be bound by a particular theory, it is believed that the use of the metallocene compound results in the formation of vinylidene olefin in the oligomerization reaction. A more preferred group of metallocene compound useful for the continuous process for making the vinylidene olefin used in the process for making neo-acid product of this disclosure are those unbridged metallocene compounds having a general formula $bisCpMX_2$, where bisCp represents two cyclopentadienyl rings, M is Zr or Hf (preferably Zr), and X is as defined above, but preferably selected from Cl, C1-C10 linear or branched alkyl groups, phenyl, and benzyl. The most preferred metallocene compound useful in the continuous process for making the vinylidene olefin having formula (F-II) is $bisCpZrCl_2$, which is commercially available and can be represented by the following formula:

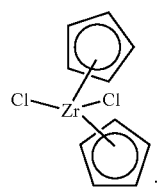

In the in the continuous process for making the vinylidene olefin having formula (F-II), the terminal olefin monomer (or multiple co-monomers) are fed into the oligomerization reactor at a first feeding rate of R(to) moles per hour, and the metallocene compound is fed into the reactor at a second feeding rate of R(mc) moles per hour. To achieve a high conversion of the terminal olefin monomer and a low selectivity of the terminal olefin toward trimer of the monomer of at most 5% (hence a high selectivity of the terminal olefin toward dimer) in the oligomerization reaction, it is highly desirable that the ratio of the first feeding rate to the second feeding rate R(to)/R(mc) be in the range from x1 to x2, where x1 and x2 can be, independently, 100, 150, 200, 250, 300, 350, 400, 450, 500, 550, 600, 650, 700, 750, 800, 850, 900, 950, or 1,000, as long as x1<x2. Preferably x1=300, and x2=800. More preferably x1=400, and x2=750. Still more preferably x1=500, and x2=750. If the ratio of R(to)/R(mc) is higher than 1,000, the conversion of the terminal olefin monomer in the oligomerization reaction can be too low. If the ratio of R(to)/R(mc) is lower than 100, the consumption of the metallocene compound can be too large, which is also undesirable.

It is highly desirable that the metallocene compound is dissolved or dispersed in an inert solvent and then fed into the reactor as a solution or a dispersion. Such inert solvent for the metallocene compound can be, e.g., benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

One or more metallocene compound(s) may be used in the continuous process for making the vinylidene olefin having formula (F-II).

I.2c The Alumoxane

The alumoxane used in the process of this disclosure functions as activator of the metallocene compound and scavenger for impurities (such as water). Alumoxanes can be obtained by partial hydrolysis of alkyl aluminum compounds. Thus, non-limiting examples of alumoxanes useful in the process of this disclosure include those made by partial hydrolysis of trimethyl aluminum, triethyl aluminum, tri(n-propyl)aluminum, tri(isopropyl)aluminum, tri(n-butyl) aluminum, tri(isobutyl)aluminum, tri-(tert-butyl)aluminum, tri(n-pentyl)aluminum, tri(n-hexyl)aluminum, tri(n-octyl) aluminum, and mixtures thereof. Preferred alumoxane for the process of this disclosure is methylalumoxane ("MAO") made from partial hydrolysis of trimethyl aluminum.

The alumoxane feed supplied into the continuously operated oligomerization reactor is advantageously substantially free of metal elements other than aluminum, alkali metals, alkaline earth metals, and the metal(s) contained in the metallocene compound(s) described above. Preferably, the alumoxane feed used in the process of this disclosure comprises metal elements other than aluminum, alkali metals, alkaline earth metals, Zr, and Hf at a total concentration of no greater than x1 ppm by mole, based on the total moles of all metal atoms in the alumoxane feed, where x1 can be 50,000, 40,000, 30,000, 20,000, 10,000, 8,000, 6,000, 5,000, 4,000, 2,000, 1,000, 800, 600, 500, 400, 200, 100, 80, 60, 50, 40, 20, or even 10. More preferably, the alumoxane feed used in the process of this disclosure comprises metal elements other than aluminum, Zr, and Hf at a total concentration of no greater than x2 ppm by mole, based on the total moles of all metal atoms in the alumoxane feed, where x2 can be 50,000, 40,000, 30,000, 20,000, 10,000, 8,000, 6,000, 5,000, 4,000, 2,000, 1,000, 800, 600, 500, 400, 200, 100, 80, 60, 50, 40, 20, or even 10. Still more preferably, the alumoxane feed fed into the reactor is free of all metals other than aluminum and the metal(s) contained in the metallocene compound(s) described above. Ions or compounds of metal elements other than aluminum, alkali metals and alkaline earth metals can be Lewis acids capable of catalyzing undesired polymerization of the terminal olefin monomer, the dimer and higher oligomers, resulting in the production of undesired 1,2-di-substituted vinylenes and tri-substituted vinylenes. Lewis acids such as metal ions can also catalyze the isomerization of the terminal olefin monomer and the isomerization of the vinylidene olefin dimer and higher oligomers, resulting in the production of internal olefin isomers of the terminal olefin monomer, 1,2-di-substituted vinylene and tri-substituted vinylene dimers and higher oligomers, which is undesirable for many applications of the oligomer product, including but not limited to the dimer product.

Preferably the alumoxane used in the continuous process for making the vinylidene olefin having formula (F-II) is substantially free of any Lewis acid capable of catalyzing the isomerization of the terminal olefin monomer, isomerization of a vinylidene olefin dimer, and polymerization of the terminal olefin monomer via mechanism differing from the oligomerization catalyzed by the metallocene compound used herein. For the purpose of this disclosure, the metallocene compound per se, the alumoxane per se, and any variations and derivatives thereof during the oligomerization reaction are not considered as Lewis acids.

A portion or the entirety of the alumoxane fed into the continuously operated oligomer reactor may be mixed with a portion or the entirety of the metallocene compound(s) described above, preferably dissolved and/or dispersed into an inert solvent, before it is fed into the reactor. In such case, the stream carrying a portion or the entirety of alumoxane fed into the reactor may contain the metal element(s) contained in the metallocene compound(s).

The alumoxane may be supplied into the reactor as a stream separate from the terminal olefin monomer stream and the metallocene compound stream. Alternatively or in addition, at least a portion of the alumoxane may be combined with the terminal olefin monomer and supplied into the reactor together. Mixing alumoxane with the olefin monomer before being supplied into the reactor can result in the scavenging of catalyst poisons contained in the monomer feed before such poisons have a chance to contact the metallocene compound inside the reactor. It is also possible to combine at least a portion of the alumoxane with at least a portion of the metallocene compound in a mixture, and supply the mixture as a catalyst stream into the reactor.

The alumoxane is desirably dissolved or dispersed in an inert solvent before being fed into the reactor or before being combined with the monomer feed and/or the metallocene compound. Mention of non-limiting examples of such inert solvent can be made of the following: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

I.2d Oligomerization Reaction Conditions

In the continuous process for making the vinylidene olefin having formula (F-II), the terminal olefin monomer (or multiple co-monomers) is fed into the oligomerization reactor at a first feeding rate of R(to) moles per hour, and the metallocene compound is fed into the reactor at a second feeding rate of R(mc) moles per hour, and the alumoxane is fed into the reactor at a third feeding rate corresponding to R(Al) moles of aluminum atoms per hour.

To achieve a high conversion of the terminal olefin monomer and a low selectivity of the terminal olefin toward trimer of the monomer of at most 5% (hence a high selectivity of the terminal olefin toward dimer) in the oligomerization reaction, it is highly desirable that the ratio of the third feeding rate to the second feeding rate R(Al)/R(mc) be in the range from y1 to y2, where y1 and y2 can be, independently, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, as long as y1<y2. Preferably y1=2.0, and y2=12.0. More preferably y1=2.0, and y2=10.0. Still more preferably y1=2.0, and y2=7.0. Still more preferably y1=2.0, and y2=5.0. If the ratio of R(Al)/R(mc) is higher than 15.0, selectivity of the terminal olefin toward trimer and higher oligomers can be too high. If the ratio of R(Al)/R(mc) is lower than 1.0, the conversion of the terminal olefin monomer in the oligomerization reaction can be too low.

The oligomerization reaction in the process of this disclosure advantageously is carried out at a mild temperature in the range from t1 to t2° C., where t1 and t2 can be, independently, 30, 35, 40, 45, 50, 55, 60, 65, 70, 75, 80, 85, or 90, as long as t1<t2. Preferably t1=40, and t2=80. More preferably t1=50, and t2=75. If the temperature is below 30° C., the reaction kinetics can be too slow. If the temperature is higher than 90° C., selectivity of the terminal olefin toward trimer and higher oligomers can be too high and the catalyst activity may be too low.

The oligomerization reaction may be carried out at a residence time in the range from rt1 to rt2 hours, where rt1 and rt2 can be, independently, 1.0, 1.5, 2.0, 2.5, 3.0, 3.5, 4.0, 4.5, 5.0, 5.5, 6.0, 6.5, 7.0, 7.5, 8.0, 8.5, 9.0, 9.0, 10, 12, 15, 18, 24, 30, 36, 42, or 48, as long as rt1<rt2. Preferably rt1=3 and rt2=8. More preferably rt1=4 and rt2=8. Still more preferably rt1=5 and rt2=7.

The oligomerization reaction is preferably carried out in the presence of mechanical stirring of the reaction mixture such that a substantially homogeneous reaction mixture with a steady composition is withdrawn from the reactor once the reactor reaches steady state.

Advantageously the oligomerization reaction of the process of this disclosure is carried out under mild pressure. Because the oligomerization reaction is sensitive to water and oxygen, the reactor is typically protected by an inert gas atmosphere such as nitrogen. To prevent air leakage into the reactor, it is desirable that the total pressure inside the reactor is slightly higher than the ambient pressure.

The oligomerization reaction can be carried out in the presence of a quantity of inner solvent. Non-limiting examples of such solvent include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

Due to the nature of the metallocene compound and the alumoxane used in the process of this disclosure, in the oligomerization reaction, a high selectivity of the terminal olefin toward vinylidenes olefins (e.g., at least 95%, 96%, 97%, 98%, or even 99%) and a low selectivity of the terminal olefin toward internal olefins including 1,2-di-substituted vinylenes and tri-substituted vinylenes (e.g., at most 5%, 4%, 3%, 2%, or even 1%) can be achieved. Thus, the oligomers thus made, especially the dimer, tend to be predominantly vinylidene and can be advantageously used as a vinylidene without further purification in applications where vinylidenes are desired.

As a result of the use of a continuous process, and the use of a metallocene compound and an alumoxane in the respective quantities above, we were able to achieve extremely low selectivity of the terminal olefin of the terminal olefin monomer toward trimer in the oligomerization reaction of at most 5%, thereby achieving a high selectivity of the terminal olefin toward the intended dimer. In certain embodiments, selectivity of the terminal olefin toward trimer can reach no greater than 4%, no greater than 3%, no greater than 2%, or even no greater than 1%. At such low selectivity of the terminal olefin toward trimer, selectivity of the terminal olefin toward tetramer and even higher oligomers are even lower and in many embodiments negligible. Thus, in the oligomerization reaction of the process of this disclosure, the selectivity of the terminal olefin toward tetramer and higher oligomers is typically no greater than 2%, or no greater than 1%, or no greater than 0.5%, or even no greater than 0.1%. Thus, in the oligomerization reaction of the process of this disclosure, the selectivity of the terminal olefin toward dimer can be at least 90% (or ≥91%, ≥92%, ≥93%, ≥94%, ≥95%, ≥96%, ≥97%, ≥98%, or even ≥99%).

In addition to the high selectivity of the terminal olefin monomer toward dimer in the oligomerization reaction, the process of this disclosure also exhibits a high conversion of the terminal olefin monomer, e.g., a conversion of at least 40%, 45%, 50%, 55%, 60%, 65%, or 70%, can be achieved in a single pass oligomerization reaction. With recycling of unreacted monomer separated from the oligomerization reaction mixture to the oligomerization reactor, the overall conversion can be even higher, making the process of this disclosure particular economic.

Because the alumoxane introduced into the reaction system in the process of this disclosure is substantially free of metals other than aluminum, metals contained in the metallocene compound, alkali metals, and alkaline earth metals, the terminal olefin monomer does not undergo significant isomerization reaction. Likewise, the isomerization of the vinylidene dimers and higher oligomers to form 1,2-di-substituted vinylene and tri-substituted vinylene is substantially avoided as well.

I.2e Post-Oligomerization Treatment

The oligomerization reaction mixture stream withdrawn from the reactor typically comprises the unreacted terminal olefin monomer, the intended dimer, trimer, tetramer and higher oligomers, the metallocene compound, the alumoxane, and optional solvent.

Once the oligomerization reaction mixture stream leaves the reactor, typically a stream of quenching agent is injected into the stream to terminate the oligomerization reactions. Non-limiting examples of quenching agents include: water, methanol, ethanol, $CO_2$, and mixtures thereof. A particularly desirable quenching agent is water.

The metal elements contained in the oligomerization mixture, including aluminum and Zr or Hf, needs to be removed from the mixture. Removal thereof can be achieved through mechanical filtration using a filtration aid such as Celite. Presence of aluminum in the liquid mixture can cause isomerization of the monomer and dimer during subsequently processing steps, such as distillation to remove the unreacted monomers and the optional distillation to remove higher oligomers such as trimers and tetramers in rare cases where the purity requirement for the dimer is so high that even the small quantity of trimer and higher oligomers produced in the continuous process for making the vinylidene olefin having formula (F-II) is considered excessive. It is highly desirable that upon filtration, the liquid mixture contains aluminum at a concentration no higher than 50 ppm by weight (preferably no higher than 30 ppm, still more preferably no higher than 20 ppm, still more preferably no higher than 10, still preferably no higher than 5 ppm), based on the total weight of the liquid mixture.

Upon filtration, a mixture comprising monomer, the desired dimer, the trimer and higher oligomers and the optional solvent is obtained. The monomer and solvent can be removed by flashing or distillation at an elevated temperature and/or optionally under vacuum. Because isomerization of the monomer is avoided in (i) in the oligomerization reaction due to the lack of Lewis acid capable of catalyzing isomerization reaction and (ii) in the flashing/distillation step due to the removal of aluminum and other metal elements from the liquid mixture at the earlier filtration step, the monomer reclaimed form the mixture consists essentially of the terminal olefin monomer as introduced into the reactor. As such, the reclaimed monomer can be recycled to the oligomerization reactor as a portion of the monomer stream. The thus obtained oligomer mixture absent monomer and solvent may be used as a vinylidene dimer olefin product as is due to the low percentage of trimer and higher oligomers. For certain applications where even higher purity of the dimer is desirable, one can remove the timer and higher oligomers by further separation such as distillation.

I.2f the Vinylidene Dimer Product

The dimer product as a result of the continuous process for making the vinylidene olefin having formula (F-II)

advantageous comprises dimer(s) of the monomer(s) as the predominant component, and trimers at a concentration no higher than 5 wt % (preferably ≤4 wt %, ≤3 wt %, ≤2 wt %, ≤1 wt %, or even ≤0.5 wt %), based on the total weight of the dimer product. Advantageously, the dimer product comprises dimer at a concentration of at least 90% (or ≥91%, ≥92%, ≥93%, ≥94%, ≥95%, ≥96%, ≥97%, ≥98%, or even ≥99%), based on the total weight of the dimer product.

The dimer product as a result of the continuous process for making the vinylidene olefin having formula (F-II) can advantageous comprise vinylidene(s) at a total concentration of at least 95 wt % (preferably ≥96 wt %, ≥97 wt %, ≥98%, or even ≥99 wt %), based on the total weight of the dimer product.

The vinylidene dimer product obtainable from the process of this disclosure can advantageously comprise one of the following compounds at a concentration of at least 95 wt %, at least 96 wt %, at least 97 wt %, at least 98 wt %, or even at least 99 wt %, based on the total weight of the dimer product, if a substantially pure terminal olefin (with a concentration of at least 95 wt %, 96 wt %, 97 wt %, 98 wt %, or 99 wt % of the terminal olefin, based on the total weight of the terminal olefins included in the monomer feed) is utilized as the monomer feed: 3-methylenepentane (from 1-butene); 4-methylenenonane (from 1-pentene); 5-methyleneundecane (from 1-hexene); 6-methylenetridecane (from 1-heptene); 7-methylenepentadecane (from 1-octene); 8-methyleneheptadecane (from 1-nonene); 9-methylenenonadecane (from 1-decene); 11-methylenetricosane (from 1-dodecene); 13-methyleneheptacosane (from 1-tetradecene); 15-methylenehentriacontane (from 1-hexadecene); 17-methyleneheptatriacontane (from 1-octadecene); and 19-methylenenonatriacontane (from 1-iscocene).

The high-purity, predominantly dimer, predominantly vinylidene product resulting from the continuous process for making the vinylidene olefin having formula (F-II) can then be advantageously used as is as a high-purity organic compound in many applications, including in the hydroformylation reaction to make the neo-acid product in this disclosure.

II. Carboxylation of the Vinylidene Olefin to Make the Neo-Acid Product

In this disclosure, Koch chemistry is employed to make neo-acids from the vinylidene olefins described above. The Koch chemistry involves a step (called "carboxylation" herein) of reacting the olefin with carbon monoxide in the presence of a strong acid at effective reaction temperature and an effective partial pressure of CO. Typically in a subsequent step the reaction mixture from the carboxylation step of reacting with CO is allowed to contact with water to produce a carboxylic acid. It is highly desirable that the step of reacting the vinylidene olefin with CO is carried out in a batch reactor due to the pressurized nature. The reactions can be schematically illustrated as follows:

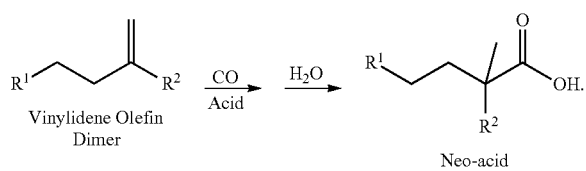

II.1 The Acid Catalyst

The acid catalyst used in the carboxylation step can be any strong organic or inorganic acids. Non-limiting examples are: (i) Brφnsted acids such as HF; HCl; sulfuric acid; phosphorous acid; and mixtures thereof; (ii) solid acids such as activated clay; acid clay; faujasite; zeolites such as X-type zeolite, Y-type zeolite, and mordenite; oxides of transition metals such as zirconium, titanium, vanadium, tungsten, molybdenum, niobium, tantalum, and mixtures and compounds thereof; and combinations and mixtures thereof; (iii) acid resins; (iv) Lewis acids such as $BF_3$, $AlCl_3$, and the like; and (v) any mixture and combination of any of categories (i), (ii), and (iii), such as HF and $BF_3$ mixture.

The amount of the acid catalyst used expressed in terms of molar ratio of the catalyst to the vinylidene olefin can range from r1 to r2, where r1 and r2 can be, independently, 0.01, 0.02, 0.04, 0.0.05, 0.06, 0.08, 0.1, 0.2, 0.4, 0.5, 0.6, 0.8, 1, 2, 4, 5, 6, 8, 10, 20, 40, or 50, as long as r1<r2. Preferably r1=0.02 and r2=80. More preferably r1=0.05 and r2=50. Still more preferably r1=0.1 and r2=10. Still more preferably r1=0.2 and r2=5. The quantity of the catalyst by mole means the quantity by mole of molecules, ions, or functional groups that provide the catalytic effect in the carboxylation reaction between the vinylidene olefin and CO in the catalyst material. Thus, the quantity by mole of a $BF_3$ catalyst means the quantity by mole of $BF_3.1.1H_2O$. $BF_3.2H_2O$ is believed to be not catalytically effective for the reaction between the vinylidene olefin and CO. However, subsequent addition of anhydrous $BF_3$ into the reaction system can convert $BF_3.2H_2O$ into catalytically active form $BF_3.1.1H_2O$. Thus in the present disclosure, where $BF_3.2H_2O$ and anhydrous $BF_3$ are introduced into the reaction system separately at stoichiometric quantities to form $BF_3.1.1H_2O$, it is assumed that all $BF_3$ is present in the reaction system in the form of $BF_3.1.1H_2O$ for the purpose of calculating the molar quantity of the $BF_3$ catalyst, and the acid catalyst is only added at the time when anhydrous BF3 is introduced into the reaction system. The quantity of a HF catalyst by mole means the quantity by mole of protons provided by the catalyst (considered as equal to the quantity of HF because of the strong acidity of HF). For solid-phase catalyst materials such as the zeolites, solid acids and acidic resins, the quantity by mole means the quantity by mole of the functional groups or ions provided by the catalyst material.

Because the olefin can undergo oligomerization in the presence of the acid catalyst, in addition to the reaction pursuant to Koch chemistry, it is highly desirable that the active acid catalyst is not allowed to contact the olefin until after the olefin has already formed a mixture with CO at a high CO partial pressure in the reaction mixture. Thus, it is desirable that the active acid catalyst is added to the reaction system only after the partial pressure of CO in the reaction system has reached 2.0 mega Pascal ("MPa"), preferably 2.5 MPa, more preferably 3.0 MPa, still more preferably 3.5 kPa, still ore preferably 5.0 MPa, still more preferably 7.0 MPa.

When $BF_3$ is used as an acid catalyst for the reaction between the vinylidene olefin and CO, it is highly desirable that a quantity of $BF_3.2H_2O$ is admixed with the vinylidene olefin feed in the reactor before CO partial pressure inside the reactor is increased to 2.0 MPa and before anhydrous $BF_3$ is introduced into the reaction system. Without intending to be bound by a particular theory, it is believed that the $BF_3.2H_2O$ is not catalytically effective for the oligomerization of the vinylidene olefin or the carboxylation reaction between the vinylidene olefin and CO. As such, to catalyze the carboxylation reaction, it is desired that after the CO partial pressure has reached a certain level as mentioned above, BF$_3$ is introduced into the reactor to effect the carboxylation reaction between the vinylidene olefin and CO.

Likewise, if a Brønsted acid such as H$_2$SO$_4$, HF, or H$_3$PO$_4$ is used as the acid catalyst, it is highly desired that the acid is not introduced into the reactor until the partial pressure of CO in the reactor has reached a certain level as discussed above.

In the event a solid acid is used as the catalyst in the carboxylation reaction, it is highly desired that the solid acid catalyst is distributed in an inert dispersant and introduced into the reactor only after the partial pressure of CO inside the reactor has reached a certain level as discussed above.

In the event it is desired to elevate the temperature of the reaction medium in the reactor to a higher level in order to achieve a desired conversion and/or reaction rate, it is highly desirable that CO partial pressure inside the reactor has reactor has reached a certain level as discussed above as well. Preferably, the temperature elevation process starts after at least a portion of the active catalyst is introduced into the reactor.

The catalyst can be added to the reaction system as a solution in an inert solvent, as a substantially pure material, or as a dispersion in an inert dispersant. Non-limiting examples of the inert solvent and/or dispersant include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

II.2 The Reaction Conditions

The carboxylation reaction of the vinylidene olefin with CO is desirably conducted in the presence of an atmosphere comprising CO at an absolute partial pressure of CO in a range from p1 to p2 MPa, where pa and p2 can be 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, or 14.0, as long as p1<p2. A high total partial pressure of CO is conducive to a high conversion of the vinylidene. Desirably, the conversion of vinylidene in the carboxylation reaction is at least 70%, preferably at least 75%, more preferably at least 80%, more preferably at least 85%, more preferably at least 90%, still more preferably at least 95%.

The carboxylation reaction of the vinylidene olefin with CO is desirably conducted at a temperature in a range from t1° C. to t2° C., where t1 and t2 can be, independently, −20, −15, −10, −5, 0, 5, 10, 15, 20, 25, 30, 35, 40, 45, 50, 55, 60, 65, 70, 75, 80, 85, 90, 95, 100, 110, or 120, as long as t1<t2. Preferably t1=0 and t2=100. More preferably t1=25 and t2=80. A higher temperature is conductive to a higher conversion and a higher reaction rate, but at the expense of selectivity toward the desired neo-acid derived from the vinylidene olefin. Reaction time can range from 0.5 hour to 96 hours, preferably 1 hour to 60 hours, more preferably no longer than 48 hours, still more preferably no longer than 36 hours, still more preferably no longer than 24 hours, still more preferably no longer than 12 hours, still more preferably no longer than 6 hours.

Given the pressurized reaction condition, it is highly desired that the carboxylation between the vinylidene olefin and CO is conducted in a batch reactor that can withstand a high internal pressure. At the end of the reaction, the reactor is cooled down and depressurized, and the carboxylation product mixture, comprising unreacted vinylidene olefin, catalyst, the desired neo-acid product, and other undesired by-products, can be advantageously separated to obtain the neo-acid product.

The carboxylation reaction between the vinylidene olefin and CO may be conducted with or without the presence of an inert solvent. Non-limiting examples of the inert solvent include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

In the step of reacting the vinylidene olefin with CO in the presence of the acid catalyst, water may be included in the reactants at a small quantity, to the extent the presence of water does not reduce the activity of the catalyst. Upon completion of reaction with CO, the reaction mixture is typically allowed to contact with water to complete the carboxylation of the vinylidene olefin to produce the desired neo-acid product. The contact with water can result in the formation of a mixture including an aqueous phase and an organic phase. The acid is typically preferentially distributed in the organic phase, and any acid catalyst soluble in water or reactive with water can be preferentially distributed in the aqueous phase. Where a solid catalyst is utilized, such as solid zeolites, solid acids, and acid resin, the catalyst can be convenient filtered from the liquid, dried and reused as appropriate in the carboxylation reaction. The neo-acid product in the organic phase may be further purified to obtain a product comprising primarily the intended acid having a formula (F-I) with desired purity. Purification can be done via one or more of water washing, solvent extraction, distillation, liquid or gas chromatography, or by using a sorbent.

In the process of the this disclosure, a high selectivity of the vinylidene olefin toward the desired neo-acid can be achieved in the carboxylation process if the catalyst is not added to the reaction until a high CO partial pressure (e.g., a partial pressure of at least 5.0, 5.5, 6.0, 6.5, or 7.0 MPa) in the reaction system has been established, resulting in a neo-acid product having a purity of the desired neo-acid after removal of the vinylidene and heavy components of at least 95 wt %, 96 wt %, at least 97 wt %, at least 98 wt %, or even at least 99 wt %, based on the total weight of the neo-acid product. Such high purity of neo-acid is very surprising.

The combination of the carboxylation process of this disclosure with the continuous process for making high-purity vinylidene dimer of a terminal olefin monomer described in detail above as the vinylidene olefin used in the carboxylation process can result in a high conversion, high selectivity process for making the desired neo-acid from a terminal olefin feed and a CO feed.

Commercially available terminal olefins useful in the process of this disclosure include but are not limited to: 1-butene, 1-pentene, 1-hexene, 1-octene, 1-decene, 1-dodecene, 1-tetradecene, 1-hexadecene, 1-octadecene, 1-icosene, and the like. They can be conveniently used to fabricate neo-acids 2-ethyl-2-methylhexanoic acid, 2-methyl-2-propylheptanoic acid, 2-butyl-2-methyloctanoic acid, 2-hexyl- 2-methyldecanoic acid, 2-methyl-2-octyldodecanoic acid, 2-decyl-2-methyltetradecanoic acid, 2-dodecyl-2-methylhexadecanoic acid, 2-methyl-2-tetradecyloctadecanoic acid, 2-hexadecyl-2-methylicosanoic acid, and 2-methyl-2-octadecyldocosanoic acid, respectively.

More preferred examples of neo-acids that can be made by the process of this disclosure include the following: 2-ethyl-2-methylhexanoic acid, 2-methyl-2-propylheptanoic acid, 2-butyl-2-methyloctanoic acid, 2-hexyl-2-methyldecanoic acid, 2-methyl-2-octyldodecanoic acid, 2-decyl-2-methyltetradecanoic acid, and 2-dodecyl-2-methylhexadecanoic acid.

Where two or more terminal olefins are used as the starting materials for making vinylidene olefin feed, the feed may comprise two or more of the following vinylidene olefins such as 4-methylenenonane; 3-methylenenonane; 5-methyleneundecane; 5-methylenetridecane; 7-methylenetridecane; 7-methylenepentadecane; 9-methyleneheptadecane; 7-methyleneheptadecane; 9-methylenenonadecane; 11-methylenehenicosane; 11-methylenetricosane; 9-methylenehenicosane; 13-methylenepentacosane; 13-methyleneheptacosane; 11-methylenepentacosane; 15-methylenenonacosane; 15-methylenehentriacontane; 13-methylenenonacosane; 15-methylenetritriacontane; 17-methylenepentatriacontane; and 17-methylenetritriacontane. Preferably the vinylidene feed comprise mixtures of two or more of the foregoing differing in number of carbon atoms contained therein no greater than 8.

The above vinylidene olefin feed can be used to make a neo-acid product comprising two or more of the following neo-acid compounds: 2-methyl-2-propylheptanoic acid; 2-butyl-2-methylhexanoic acid; 2-ethyl-2-methyloctanoic acid; 2-butyl-2-methyloctanoic acid; 2-butyl-2-methyldecanoic acid; 2-hexyl-2-methyloctanoic acid; 2-hexyl-2-methyldecanoic acid; 2-methyl-2-octyldecanoic acid; 2-hexyl-2-methyldodecanoic acid; 2-methyl-2-octyldodecanoic acid; 2-decyl-2-methyldodecanoic acid; 2-decyl-2-methyltetradecanoic acid; 2-methyl-2-octyltetradecanoic acid; 2-dodecyl-2-methyltetradecanoic acid; 2-dodecyl-2-methylhexadecanoic acid; 2-decyl-2-methylhexadecanoic acid; 2-methyl-2-tetradecylhexadecanoic acid; 2-methyl-2-tetradecyloctadecanoic acid; 2-dodecyl-2-methyloctadecanoic acid; 2-methyl-2-tetradecylicosanoic acid; 2-hexadecyl-2-methylicosanoic acid; and 2-hexadecyl-2-methyloctadecanoic acid. Preferably the neo-acid product comprises mixtures of two or more of the foregoing differing in number of carbon atoms contained therein no greater than 8, more preferably no greater than 6, still more preferably no greater than 4, and still more preferably no greater than 2.

The present invention is further illustrated by the following non-limiting examples.

EXAMPLES

Part A: Dimerization of Terminal Olefins to Make Vinylidene Olefins

Example A1

Dimerization of 1-Tetradecene in a Continuous Reactor

Into a 2-gallon (6.56-liter) continuously stirred tank reactor was continuously fed 1-tetradecene feed (containing 98.6 wt % 1-tetradecene, 0.7 wt % 1-dodecene and 0.7 wt % of 1-hexadecene, and trace amounts of 1-octene and 1-decene) at a feeding rate of 3.3 moles per hour, bisCpZrCl$_2$ (dissolved or dispersed in toluene at a concentration of 1.4 wt %) at a feeding rate of 0.0048 mole per hour, and MAO (dissolved or dispersed in toluene at a concentration of 10 wt % at a feeding rate of 0.022 mole aluminum atoms per hour, operating at a constant temperature of 70° C. and residence time of 8.0 hours. The product mixture effluent exiting the reactor was immediately quenched by injecting room-temperature water at a feeding rate of 2 milliliter per hour. Filter aid was then added into the quenched product mixture. The resultant mixture was then filtered to remove solids to obtain a liquid. The liquid was then measured by gas chromatography to show a conversion of 1-tetradecene in the reaction of 71%. The liquid was then vacuum distilled at an absolute pressure of 4 mmHg (533 Pascal) to obtain a clear residual liquid as the final product. The final product was then characterized by gas chromatography to show the following composition, with total concentration of dimers at 98.84 wt %.

| Components | | Concentration (wt %) |
|---|---|---|
| C14 monomer | | <0.10 |
| Dimers | C16-C26 | 1.69 |
| | C28-C32 | 97.15 |
| | C16-C32 | 98.84 |
| Trimers (C36-C48) | | 0.86 |
| Tetramers (C48-C64) | | 0.24 |

The final product was then characterized by $^1$H NMR. Data show that the final product was predominantly 13-methyleneheptacosane. Data showed the presence of vinyls, vinylidenes, 1,2-di-substituted vinylenes, and tri-substituted vinylenes. The vinyls are attributed to residual 1-tetradecene monomer. The remaining olefin types (1,2-di-substituted vinylenes, tri-substituted vinylenes, and vinylidenes) were normalized to sum up to 100%. Their respective distributions are given below.

| Olefin Type | Concentration (mol %) |
|---|---|
| 1,2-Di-substituted Vinylenes | 1.1 |
| Tri-substituted Vinylenes | 1.1 |
| Vinylidenes | 97.8 |

Clearly, in the CSTR process of this Example A1, a high-purity, predominantly vinylidene olefin dimer product was produced. Because of the low concentrations of heavy components such as trimers and tetramers, the final product can be used as a vinylidene olefin dimer for many applications without further distillation to remove the heavy components. The overall conversion of the monomer at 71% without recycle is quite high. The very low distribution of 1,2-di-substituted vinylenes and tri-substituted vinylenes in the final product indicates that isomerization of the vinylidene olefin dimer into either of the vinylenes occurred at an extremely low level, if at all. This is due in part to the lack of metal elements other than aluminum and zirconium that may function as a Lewis acid capable of catalyzing the isomerization of vinyls and vinylidenes to produce vinylenes. As discussed below, it is believed that the presence of metal ions such as $Cu^{2+}$ in the reaction system, which can serve as Lewis acids, can lead to dimerization of the terminal olefin through mechanism different from that catalyzed by a metallocene compound, resulting in the production of vinylenes and branched oligomers, which is highly undesirable.

Example A2 (Comparative)

Dimerization of 1-Tetradecene in a Batch Reactor

Into a 2-gallon (6.56-liter) batch reactor equipped with mechanical stirring was charged 2.2 grams (0.0076 moles) bisCpZrCl$_2$ (dissolved or dispersed in toluene at a concentration of 1 wt %), followed by 1.74 grams of MAO (corresponding to 0.030 moles of aluminum atoms) dissolved or dispersed in toluene at a concentration of 10 wt %, and lastly added 4.4 kilograms (22.4 moles) of 1-tetradecene feed (containing 98.6 wt % 1-tetradecene, 0.7 wt % 1-dodecene and 0.7 wt % of 1-hexadecene, and trace amounts of 1-octene and 1-decene) over a period of 90 minutes. The reactor was then operated at a constant reaction temperature of 70° C. for a batch reaction period of 6.0 hours. The product mixture at the end of the reaction period was immediately quenched by injecting 3 grams of water. Filter aid was then added into the quenched product mixture. The resultant mixture was then filtered to remove solids to obtain a liquid. The liquid was then measured by gas chromatography to show a conversion of 1-tetradecene in the reaction to oligomers of 37%. The liquid was then vacuum distilled at an absolute pressure of 10 mmHg (1333 Pascal) to remove residual monomer and to obtain a clear residual liquid as the final product. The final product was then characterized by gas chromatography to show the following composition, with a total concentration of dimers at 95.42 wt %.

| Components | | Concentration (wt %) |
|---|---|---|
| Dimers | C16-C26 | 2.19 |
| | C28-C30 | 93.23 |
| | C16-C30 | 95.42 |
| Trimers (C36-C48) | | 3.26 |
| Tetramers (C48-C64) | | 1.32 |

In the batch process of this comparative Example A2, the conversion of the linear terminal olefin monomer was much lower than in the continuous process of Example A1, even though the overall loading of the metallocene compound and MAO were comparable. In addition, the final product after the removal of residual monomer resulting from this batch process also contained trimers and tetramers at concentrations more than twice that in the final product from the continuous process of Example A1. The continuous process of Example A1 was far superior in producing a high-purity vinylidene olefin dimer product from a linear terminal olefin such as 1-tetradecene.

Example A3 (Comparative)

Dimerization of 1-Tetradecene in a Batch Reactor

This experiment was carried out in substantially the same manner and sequence as in comparative Example A2, with the exception that the monomer feed was added first, followed by the addition of MAO solution at the same quantity and a holding period of 1 hour, before the metallocene compound solution at the same quantity was finally added. Catalyst loadings, temperature and reaction time remained the same as in Example A2. The conversion of monomer to oligomer product was measured to be 59%, slightly higher than Example A2, but still much lower than in Example A1. The final product was measured to have the following composition.

| Components | | Concentration (wt %) |
|---|---|---|
| Dimers | C16-C26 | 1.65 |
| | C28-C30 | 84.42 |
| | C16-C30 | 86.07 |
| Trimers (C36-C48) | | 6.25 |
| Tetramers (C48-C64) | | 7.68 |

In this batch process of comparative Example A3, selectivity of the terminal olefin toward dimers in the reaction was reduced to a mere 86.07%, resulting in large quantities of trimers and tetramers in the final product, which would have to be removed by distillation in order for the dimer to be useful as a pure product for many applications.

Example A4 (Comparative)

Dimerization of 1-Decene in a Batch Reactor

Into a 2-gallon (6.56-liter) batch reactor equipped with mechanical stirring was charged 5 kilograms (26 moles) of 1-decene feed (containing 98.8 wt % 1-decene, 0.5 wt % 1-octene, 0.7 wt % 1-dodecene, and trace amounts of 1-hexene and 1-tetradecene), followed by 5 grams MAO (corresponding to 0.086 moles Al atoms) dissolved or dispersed in toluene at a concentration of 10 wt %, and finally 6.3 grams (0.022 moles) bisCpZrCl$_2$ dissolved or dispersed in toluene at a concentration of 1.4 wt %, and held at a constant reaction temperature of 80° C. for a batch reaction period of 6.0 hours. The product mixture at the end of the reaction period was immediately quenched by injection of 10 grams of water. Filter aid was then added into the quenched product mixture. The resultant mixture was then filtered to remove solids to obtain a liquid. The liquid was then measured by gas chromatography to show a conversion of monomers in the reaction to oligomers of 77%. The liquid was then distilled under a vacuum of an absolute pressure of 10 mmHg (1333 Pascal) to remove residual monomer and to obtain a clear residual liquid as an intermediate product. The intermediate product was then characterized by gas chromatography to show the following composition.

| Components | Concentration (wt %) |
|---|---|
| C20 Dimers | 79.23 |
| C30 Trimer | 4.72 |
| C40 Tetramer | 16.05 |

In the batch process of this comparative Example A4, the conversion of the linear terminal olefin monomer was much lower than in the continuous process of Example A1, even though the overall loading of the metallocene compound and MAO were comparable. In addition, the intermediate product after the removal of residual monomer resulting from this batch process also contained trimers and tetramers at a concentration more than ten times that in the final product from the continuous process of Example A1. Such large quantity of trimer and tetramers render the intermediate product not useable directly as a dimer product for many applications. The continuous process of Example A1 was far superior in producing a high-purity vinylidene olefin dimer product from a linear terminal olefin.

A further step of distillation of the intermediate product was then performed to remove the heavy trimer and tetramer to obtain a final product of C20 dimer having the following composition as measured by gas chromatography.

| Component | Concentration (wt %) |
|---|---|
| C20 dimer | 99.36 |
| C30 trimer | 0.56 |
| C40 tetramer | 0.08 |

The final product in this example was characterized by 1H-NMR to determine the distribution of olefin types. Vinyls were quantified from the NMR spectra but assumed to be from residual monomer. The distribution of vinylidenes, 1,2-di-substituted vinylenes and tri-substituted vinylenes in the oligomers are as follows.

| Components | Concentration (mol %) |
|---|---|
| 1,2-Di-substituted Vinylenes | 1.2 |
| Tri-substituted Vinylenes | 0.7 |
| Vinylidenes | 98.1 |

Thus, in the batch process of this Example A4, exceedingly low distribution of 1,2-di-substituted vinylene and tri-substituted vinylene were produced. Without intending to be bound by a particular theory, it is believed that this is due to the lack of metal ions and Lewis acids other than the MAO and the metallocene compounds in the reaction system, and the hence the lack of isomerization of the terminal olefin monomer and the vinylidene olefin dimer that may be otherwise catalyzed by the presence of other Lewis acids.

U.S. Pat. No. 4,658,708 disclosed multiple examples in which a 1-olefin (such as propylene, 1-hexene, and 1-octene) was oligomerized in the presence of bisCpZrCl$_2$ and MAO to produce a dimer product with impressive selectivity toward dimers. Many examples in this patent reference showed significant isomerization of the 1-olefin to produce its isomer 2-olefin. No distribution data of the vinylidenes, 1,2-di-substituted vinylenes and tri-substituted vinylenes in the final product were given in the examples in this patent. The high level of isomerization of the 1-olefin indicates that there is a high likelihood that the vinylidene olefin dimer and higher oligomers isomerized to form 1,2-di-substituted vinylenes and tri-substituted vinylenes at significant quantities. The cause of the isomerization is highly likely the presence of CuSO$_4$ in the reaction systems, which was derived from the CuSO$_4$.5H$_2$O used for making the MAO. The Cu$^{2+}$ in CuSO$_4$, a Lewis acid, catalyzed the isomerization of the 1-olefin to form 2-olefin isomer, the isomerization of vinylidene oligomers to form 1,2-di-substituted vinylenes and tri-substituted vinylenes, and likely the polymerization of the 1-olefins by mechanism different from that catalyzed by bisCpZrCl$_2$, again resulting in the formation of 1,2-di-substituted vinylenes and tri-substituted vinylenes.

None of the examples in U.S. Pat. No. 4,658,708 used a continuous process.

Part B: Synthesis of 2-Methyl-2-Octyldodecanoic Acid

Example B1

Synthesis of 9-Methylenenonadecane

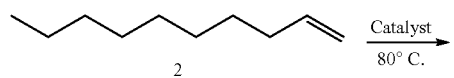

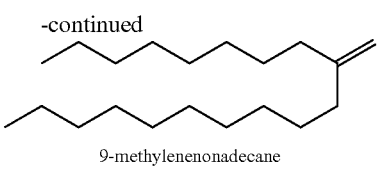

9-methylenenonadecane

Into a batch reactor was charged 5000 grams of 1-decene (98.6% decene, 0.7% octene, 0.7% dodecene), into which 50 grams of 10% MAO solution in toluene was added and held for 60 minutes at 80° C. 450 grams of catalyst solution (1.4 wt % biscyclopentadienyl zirconium (IV) dichloride dissolved in toluene) was subsequently added over 52 minutes. The reactor was held at 80° C. for 6 hours before the reaction was cooled and quenched with 10 mL of water. Gas chromatography showed reactor conversion was 74% with 88% selectivity to dimer and 12% selectivity to trimer and heavier species.

Filter aid was added thereafter into the fluid, which was filtered to remove Zr and/or Al-containing solid particles. The resultant mixture was then flashed to remove the residual monomer and distilled to remove heavies product to isolate the dimer species. The recovered dimer product was measured to contain dimers of the starting olefin at a concentration of 99.5 wt % by GC and a concentration of 9-methylenenonadecane at 98 mol % (by $^1$H NMR).

Example B2

Synthesis of 2-Methyl-2-Octyldodecanoic Acid

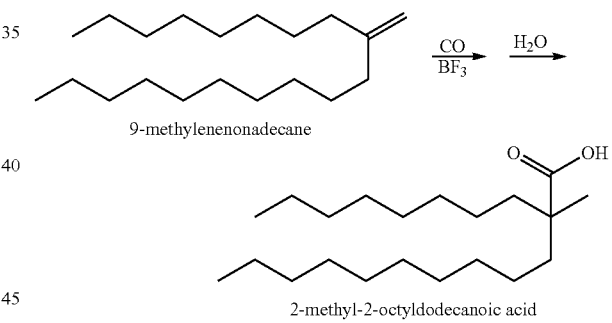

Into a 1-gallon (3.78-liter) autoclave, 1204 grams of the dimer product obtained from Example B1 above was added. Then 613 grams of BF$_3$-dihydrate was added with stirring and cooling. The reactor was then pressurized to 1000 psig with CO. Afterwards an additional 330 grams of anhydrous BF$_3$ was bubbled into the reactor. Thus it is assumed all BF$_3$-dihydrate and all of the anhydrous BF$_3$ react to form stoichiometric BF$_3$.1.1H$_2$O, the catalytically active form for the carboxylation reaction above. The reactor was then pressurized to 2000 psig (13.79 MPa, gauge pressure) by CO and the temperature of the reactor increased to 50° C. The reaction was allowed to continue for 22 hours at the same CO pressure and the same temperature. Afterwards, the reactor was depressurized and allowed to cool to 30° C.

The reaction mixture was then pressured into a 12-liter flask containing 4 liters of water. Nitrogen gas was bubbled through the mixture for 3 hours to remove residual BF$_3$. Excess water was then drained off. The resultant mixture was then water washed seven (7) times, each time using one (1) liter of deionized water to remove the residual catalyst.

Residual water in the resultant mixture was subsequently removed from with a rotary evaporator to obtain a crude product.

The total conversion of the vinylidene olefin in the carboxylation step was measured (by gas chromatography) to be 90.7%, with a yield to heavy dimer species of the vinylidene olefin measured to be 6.6%, and thus a yield to the desired neo-acid product at 84.1%.

The crude product was then batch distilled to remove lights (unreacted vinylidene olefin) and heavies to obtain a final neo-acid product. Gas chromatography of the final neo-acid product showed a concentration of neo-acid of about 98% and a concentration of heavy components of about 2%.

The final neo-acid product was measured to have a KV100 of 8.51 cSt, and a KV40 of 64.0 cSt. $^{13}$C-NMR spectra, included in FIG. 1, indicates that the final neo-acid product contained 2-methyl-2-octyldodecanoic acid at a purity of 98.1 wt %.

Example B3

Into a 1-gallon (3.78-liter) autoclave, 1198 grams of the dimer product from Example B1 was added. Then, 818 grams of $BF_3$-dihydrate was added with stirring and cooling. The reactor was then pressurized to 400 psig with CO. Afterwards, additional 440 grams of $BF_3$ was bubbled into the reactor. Upon completion of the addition of the $BF_3$ catalyst, the reactor was then pressurized by CO to a pressure of 2000 psig (13.79 MPa, gauge pressure). The temperature of the reactor increased to 50° C. The reaction was allowed to continue for 22 hours at the same CO pressure and same temperature. Then the reactor was depressurized and allowed to cool down to 30° C.

To form the carboxylic acid product, the resultant mixture was then pressured into a 12-liter flask containing 4 liters of water. Nitrogen gas was bubbled through the mixture for 3 hours to remove residual $BF_3$. Excess water was then drained off. The resultant reaction mixture was water washed seven (7) times using one (1) liter of deionized water each time to remove residual $BF_3$. Residual water was removed from the washed mixture with a rotary evaporator to obtain a crude product.

The conversion of olefin to carboxylic acid in the carboxylation reaction was measured to be 76.0%, with a yield to heavy dimer species of the vinylidene olefin measured to be 11.8%, and thus a yield to the desired neo-acid product at 64.2%.

Example B4

Into a 1-gallon (3.78-liter) autoclave, 1203 grams of the dimer product of Example B1 was added. Then 818 grams of $BF_3$-dihydrate was added with stirring and cooling. Afterwards an additional 441 grams of $BF_3$ was bubbled into the reactor, which increased the reactor pressure to 340 psig (2.34 MPa, gauge pressure). Upon completion of the addition of $BF_3$ catalyst, CO was slowly introduced into the reactor until a pressure of 2000 psig (13.79 MPa, gauge pressure) was reached. The temperature of the reactor increased to 50° C. The reaction was allowed to continue for 22 hours at the same CO pressure and the same temperature. Then the reactor was depressurized and allowed to cool down to room temperature.

The reaction mixture was then pressured into a 12-liter flask containing 4 liters of water. Nitrogen gas was bubbled through the mixture for 3 hours to remove residual $BF_3$. Excess water was then drained off. The resultant mixture was then water washed seven (7) times using one (1) liter of deionized water each time in order to remove the residual $BF_3$ catalyst. Residual water was removed from the reactor effluent with a rotary evaporator to obtain a crude product.

The conversion of olefin to carboxylic acid in this reaction was measured to be 35.9% with a yield to heavy dimer species of the vinylidene olefin measured to be 34.6%, and thus a yield to the desired neo-acid product at 1.3%.

Results Discussion

The three examples are summarized as follows.

| | | Example | | |
|---|---|---|---|---|
| | | B2 | B3 | B4 |
| | | | Loading Procedure | |
| | | Added CO to achieve a total pressure of 1000 psig before adding $BF_3$ | Added CO to achieve a total pressure of 400 psig before adding $BF_3$ | No CO was introduced into reactor before adding $BF_3$ |
| Catalyst to vinylidene ratio | (weight) | 0.78 | 1.05 | 1.05 |
| Maximal Reactor Pressure | (Psig) | 2000 | 2000 | 2000 |
| Reaction Temperature | (° C.) | 50 | 50 | 50 |
| Reaction time | (Hours) | 22 | 22 | 22 |
| Conversion of Vinylidene | (wt %) | 90.7 | 76.0 | 35.9 |
| Yield of Heavies | (wt %) | 6.6 | 11.8 | 34.6 |
| Yield of Neo-Acid | (wt %) | 84.2 | 64.2 | 1.3 |

One can see the preferred loading procedure involves adding CO to the reactor until a high partial pressure thereof of at least 400 psig (2.76 MPa, gauge pressure) total pressure in the reactor is achieved prior to adding gaseous $BF_3$, which resulted in much higher conversion of the vinylidene and a much higher yield to the desired neo-acid product. Without intending to be bound by a particular theory, it is believed that without the presence of CO at a sufficient partial pressure, the presence of $BF_3$ at substantial quantity results in the dimerization of the vinylidene olefin to form an undesired byproduct. It is known that $BF_3$ can catalyze oligomerization of olefins via a cationic reaction mechanism. Thus, raising the partial pressure of CO in the reaction system to a high level, e.g., of at least 500 psig (3.45 MPa, gauge pressure), 600 psig (4.14 MPa, gauge pressure), 800 psig (5.12 MPa, gauge pressure), 1000 psig (6.89 MPa, gauge pressure), 1200 psig (8.27 MPa, gauge pressure), 1400 psig (9.65 MPa, gauge pressure), 1500 psig (10.34 MPa, gauge pressure), 1600 psig (11.03 MPa, gauge pressure), 1800 psig (12.41 MPa, gauge pressure), and 2000 psig (13.79 MPa, gauge pressure) before the introduction of BF$_3$ into the reaction system lead to the preferred reaction between the vinylidene olefin and CO once BF$_3$ is introduced, resulting in a much higher conversion of the vinylidene and a much higher selectivity toward the desired neo-acid product.

What is claimed is:

1. A compound having a formula (F-I) below:

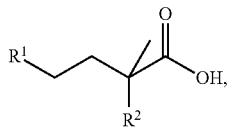
(F-I)

wherein R$^1$ and R$^2$ are a C6 to C30 linear or branched alkyl group and R$^1$ and R$^2$ are identical.

2. The compound of claim 1, wherein R$^1$ and R$^2$ are a linear alkyl group.

3. The compound of claim 1, wherein R$^1$ and R$^2$ are selected from n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl.

4. The compound of claim 2, wherein R$^1$ and R$^2$ are selected from n-hexyl, n-octyl, n-decyl, and n-dodecyl.

5. The compound of claim 1, which is selected from: 2-hexyl-2-methyldecanoic acid; 2-methyl-2-octyldodecanoic acid; 2-decyl-2-methylhexadecanoic acid; 2-decyl-2-methyldecanoic acid; 2-dodecyl-2-methyldecanoic acid; 2-methyl-2-tetradecylocotadecanoic acid; and 2-hexadecyl-2-methylicosanoic acid.

6. A process for making a neo-acid product comprising a neo-acid compound having a formula (F-I) below:

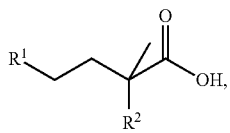
(F-I)

wherein R$^1$ and R$^2$ are each independently a hydrocarbyl group comprising at least two carbon atoms, the process comprising:
(I) providing a vinylidene olefin feed comprising a vinylidene olefin having a formula (F-II) below:

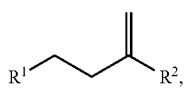
(F-II)

where R$^1$ and R$^2$ correspond to the R$^1$ and R$^2$ in formula (F-I) above, respectively;
(II) contacting the vinylidene olefin with carbon monoxide in a reactor in the presence of an active acid catalyst to obtain a reaction mixture; wherein the active acid catalyst is not added into the reactor until after the partial pressure of carbon monoxide (CO) in the reactor has reached 2.0 MPa;
(III) contacting the reaction mixture with water to obtain an acid product mixture; and
(IV) obtaining the neo-acid product from the acid product mixture.

7. The process of claim 6, wherein in step (II), the active acid catalyst is not added into the reactor until after the partial pressure of carbon monoxide in the reactor reaches at least 3.5 MPa.

8. The process of claim 6, wherein in step (II), the active acid catalyst is not added into the reactor until after the partial pressure of CO in the reactor has reached 5.0 MPa.

9. The process of claim 6, wherein steps (II) and (III) combined have a selectivity of the vinylidene olefin toward the neo-acid compound of at least 90% after removal of vinylidene and heavy components.

10. The process of claim 6, wherein R$^1$ and R$^2$ are each independently a C2 to C30 linear or branched alkyl group.

11. The process of claim 6, wherein R$^1$ and R$^2$ are each independently a linear alkyl group.

12. The process of claim 6, wherein R$^1$ and R$^2$ are identical.

13. The process of claim 6, wherein in step (I), the vinylidene olefin feed consists essentially of a single vinylidene olefin having a formula (F-II).

14. The process of claim 6, wherein in step (I), the vinylidene olefin feed comprises multiple vinylidene olefins each having a different formula (F-II), and the multiple vinylidene olefins differ in terms of molecular weight thereof by no more than 150 grams per mole.

15. The process of claim 6, wherein in step (I), the vinylidene olefin is selected from: 4-methylenenonane; 3-methylenenonane; 5-methyleneundecane; 5-methylenetridecane; 7-methylenetridecane; 7-methylenepentadecane; 9-methyleneheptadecane; 7-methyleneheptadecane; 9-methylenenonadecane; 11-methylenehenicosane ; 11-methylenetricosane; 9-methylenehenicosane; 13-methylenepentacosane ; 13-methyleneheptacosane; 11-methylenepentacosane; 15-methylenenonacosane ; 15-methylenehentriacontane; 13-methylenenonacosane; 15-methylenetritriacontane; 17-methylenepentatriacontane; 17-methylenetritriacontane; and any mixtures of two or more of the foregoing differing in number of carbon atoms contained therein no greater than 8.

16. The process of claim 6, wherein step (I) comprises the following steps:
(Ia) providing a monomer feed comprising a terminal olefin having a formula (F-III) below and optionally a terminal olefin having a formula (F-IV) below: R$^1$-CH=CH$_2$ (F-III), R$^2$—CH=CH$_2$(F-IV), where R$^1$ and R$^2$ correspond to the R$^1$ and R$^2$ in formula (F-I), respectively;
(Ib) oligomerizing the monomer feed in an oligomerization reactor in the presence of a catalyst system comprising a metallocene compound to obtain an oligomerization product mixture; and
(Ic) obtaining at least a portion of the vinylidene olefin feed from the oligomerization product mixture.

17. The process of claim 16, wherein in step (Ia), the monomer feed comprises a single terminal olefin having a formula (F-III).

18. The process of claim 16, wherein in step (Ia), the monomer feed comprises both the terminal olefin having formula (F-III) and the terminal olefin having formula (F-IV), and the two terminal olefins differ in terms of molecular weight thereof by no more than 100 grams per mole.

19. The process of claim 16, wherein:
in step (Ib), the metallocene compound has a formula $Cp(Bg)_nMX_2Cp'$, wherein M is selected from Hf and Zr; each X is independently a halogen or a hydrocarbyl group; Cp and Cp', the same or different, independently represents a cyclopentadienyl, alkyl-substituted cyclopentadienyl, indenyl, alkyl-substituted indenyl, 4,5,6,7-tetrahydro-2H-indenyl, alkyl-substituted 4,5,6,7-tetrahydro-2H-indenyl, 9H-fluorenyl, and alkyl-substituted 9H-fluorenyl; each Bg is a bridging group covalently linking Cp and Cp'; and n is 0, 1, or 2; and the catalyst system further comprises an alumoxane.

20. The process of claim 19, wherein:
step (Ib) is carried out in a continuous process at a temperature in the range from 50 to 90° C.; and in step (Ib):
the metallocene compound is fed into the oligomerization reactor at a feeding rate of R(mc) moles per hour, the alumoxane is fed into the oligomerization reactor at a feeding rate of R(Al) moles per hour, the monomer is fed into the oligomerization reactor at a feeding rate of R(to) moles per hour, $350 \leq R(to)/R(mc) \leq 750$, $2 \leq R(Al)/R(mc) \leq 10$, an oligomer mixture comprising the vinylidene olefin and a trimer of the terminal olefin is produced, and the selectivity toward the trimer is less than 5%.

21. The process of claim 6, wherein the active acid catalyst in step (II) is selected from a Brønsted acid, a solid acid, an acidic resin, a Lewis acid, and mixtures and combinations thereof.

22. The process of claim 6, wherein the active acid catalyst comprises $BF_3 \cdot 1.1H_2O$.

23. The process of claim 6, wherein in step (II), the molar ratio of the active acid catalyst to the vinylidene olefin is in the range from 0.01 to 50.

24. The process of claim 6, wherein in step (II), the vinylidene olefin is admixed with $BF_3 \cdot 1.2H_2O$ before the partial pressure of CO in the reactor has reached 2.0 MPa, and afterwards $BF_3$ is added into the reactor to form active acid catalyst $BF_3 \cdot 1.1H_2O$.

25. The process of claim 6, wherein step (II) further comprises raising the reaction pressure to at least 7 MPa after adding the active acid catalyst.

26. The process of claim 6, wherein step (II) further comprises raising the reaction temperature to at least 50° C. after adding the active acid catalyst.

27. The process of claim 6, wherein steps (II) and (III) combined have a yield of the vinylidene olefin toward the neo-acid compound of at least 64%.

28. The process of claim 6, wherein steps (II) and (III) combined have a yield of the vinylidene olefin toward the neo-acid compound of at least 84%.

29. The process of claim 9, wherein removal of vinylidene and heavy components comprises one or more of the following processes, water washing, solvent extraction, distillation, liquid or gas chromatography, and a sorbent.

30. The process of claim 29, wherein removal of vinylidene and heavy components comprises distillation.

* * * * *